United States Patent
O'Malley

(10) Patent No.: US 12,029,442 B2
(45) Date of Patent: Jul. 9, 2024

(54) SYSTEMS AND METHODS FOR A DUAL ELONGATED MEMBER CLOT RETRIEVAL APPARATUS

(71) Applicant: Neuravi Limited, Galway (IE)

(72) Inventor: Thomas O'Malley, Westport (IE)

(73) Assignee: NEURAVI LIMITED, Galway (IE)

( * ) Notice: Subject to any disclaimer, the term of this patent is extended or adjusted under 35 U.S.C. 154(b) by 331 days.

(21) Appl. No.: 17/148,766

(22) Filed: Jan. 14, 2021

(65) Prior Publication Data
US 2022/0218370 A1    Jul. 14, 2022

(51) Int. Cl.
| | | |
|---|---|---|
| A61B 17/221 | (2006.01) | |
| A61B 17/00 | (2006.01) | |
| A61B 90/00 | (2016.01) | |
| A61M 25/00 | (2006.01) | |

(52) U.S. Cl.
CPC ....... *A61B 17/221* (2013.01); *A61M 25/0021* (2013.01); *A61B 2017/00867* (2013.01); *A61B 2090/3966* (2016.02); *A61M 2025/0042* (2013.01)

(58) Field of Classification Search
CPC ........ A61B 17/221; A61B 2017/00867; A61B 2090/3966; A61B 2017/22034; 2017/2212; A61B 2017/22038; A61B 17/22031; A61B 2017/22001; A61B 2017/22079; A61B 2017/22094; A61B 2017/221; A61B 2017/22035; A61B 2017/2215; A61B 2017/2217; A61B 17/22; A61M 25/0021; A61M 2025/0042; A61F 2/01; A61F 2/013; A61F 2/0103; A61F 2/0105; A61F 2/0108; A61F 2/011;
(Continued)

(56) References Cited

U.S. PATENT DOCUMENTS

| | | |
|---|---|---|
| 2,828,147 A | 12/1899 | Peiffer |
| 3,361,460 A | 1/1968 | Gerhart et al. |
| 4,455,717 A | 6/1984 | Gray |

(Continued)

FOREIGN PATENT DOCUMENTS

| | | |
|---|---|---|
| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)
Extended European Search Report issued in European Patent Application No. 22 15 1283 dated Jun. 7, 2022.

*Primary Examiner* — Brooke Labranche
*Assistant Examiner* — Nasheha Baset
(74) *Attorney, Agent, or Firm* — TROUTMAN PEPPER HAMILTON SANDERS LLP

(57) ABSTRACT

A clot removal device comprising an outer cage, an inner cage concentrically positioned within the outer cage, a first elongated member in communication with the outer cage, and a second elongated member in communication with the inner cage. The first elongated member can be attached to a proximal end of the outer cage and configured to move the outer cage between delivery and expanded configurations. The second elongated member can be attached to a proximal end of the inner cage and configured to move the inner cage between delivery and expanded configurations.

18 Claims, 7 Drawing Sheets

(58) Field of Classification Search
CPC .... A61F 2/012; A61F 2/014; A61F 2002/015; A61F 2002/016; A61F 2002/018
See application file for complete search history.

(56) References Cited

U.S. PATENT DOCUMENTS

| | | |
|---|---|---|
| 4,611,594 A | 9/1986 | Grayhack et al. |
| 4,612,931 A | 9/1986 | Dormia |
| 4,643,184 A | 2/1987 | Mobin-Uddin |
| 4,727,873 A | 3/1988 | Mobin-Uddin |
| 4,793,348 A * | 12/1988 | Palmaz ............... A61F 2/0105 606/1 |
| 4,873,978 A | 10/1989 | Ginsburg |
| 5,011,488 A | 4/1991 | Ginsburg |
| 5,084,065 A | 1/1992 | David et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,598,265 B2 | 7/2003 | Lee |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |

(56) References Cited

U.S. PATENT DOCUMENTS

| | | |
|---|---|---|
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Andau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,609,649 B1 | 10/2009 | Bhandari et al. |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |

(56) References Cited

U.S. PATENT DOCUMENTS

| | | |
|---|---|---|
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 * | 10/2017 | Harrah ................. A61B 17/221 |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gaji et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,383,644 B2 * | 8/2019 | Molaei ............. A61B 17/22031 |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,439,418 B2 | 9/2022 | O'Malley |
| 11,517,340 B2 | 12/2022 | Casey |
| 2001/0003315 A1 | 5/2001 | Bates et al. |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Pubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |

(56) References Cited

U.S. PATENT DOCUMENTS

| | | |
|---|---|---|
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zando-Azizi et al. |
| 2002/0095171 A1 | 7/2002 | Belef |
| 2002/0123765 A1 | 9/2002 | Sepetka et al. |
| 2002/0128680 A1 | 9/2002 | Pavolvic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0064151 A1 | 4/2003 | Klinedinst |
| 2003/0069520 A1 | 4/2003 | Skujins et al. |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033248 A1 | 2/2005 | Machida et al. |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0215942 A1* | 9/2005 | Abrahamson ...... A61B 17/2202 604/22 |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |

(56) References Cited

U.S. PATENT DOCUMENTS

| | | |
|---|---|---|
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1* | 6/2011 | Ferrera ............ A61B 17/12118 606/200 |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0022572 A1 | 6/2012 | Braun et al. |
| 2012/0143230 A1* | 6/2012 | Sepetka .................. A61F 2/013 606/159 |
| 2012/0143237 A1 | 6/2012 | Cam et al. |
| 2012/0143317 A1 | 6/2012 | Cam et al. |
| 2012/0150147 A1 | 6/2012 | Eynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1* | 1/2013 | Marks ..................... A61F 2/013 606/200 |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1* | 12/2013 | Brady ............ A61B 17/320725 606/200 |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |

(56) References Cited

U.S. PATENT DOCUMENTS

| | | |
|---|---|---|
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1* | 6/2014 | Eskuri .................... A61M 5/007 604/523 |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1* | 12/2014 | Vale ........................ A61F 2/013 606/200 |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | John |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | John |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |

(56) References Cited

U.S. PATENT DOCUMENTS

| | | |
|---|---|---|
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1* | 9/2020 | Choe .................. A61B 17/221 |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | | |
|---|---|---|---|
| CN | 102307613 A | 1/2012 | |
| CN | 102316809 A | 1/2012 | |
| CN | 102596098 A | 7/2012 | |
| CN | 103764049 A | 4/2014 | |
| CN | 104042304 A | 9/2014 | |
| CN | 105208950 A | 12/2015 | |
| CN | 105662532 A | 6/2016 | |
| CN | 205359559 U | 7/2016 | |
| CN | 107530090 A | 1/2018 | |
| CN | 208582467 U | 3/2019 | |
| DE | 202009001951 U1 | 3/2010 | |
| DE | 102009056450 A1 | 6/2011 | |
| DE | 102010010849 A1 | 9/2011 | |
| DE | 102010014778 A1 | 10/2011 | |
| DE | 102010024085 A1 | 12/2011 | |
| DE | 102011014586 B3 | 9/2012 | |
| EP | 1153581 A1 | 11/2001 | |
| EP | 2301450 A1 | 3/2011 | |
| EP | 2438891 A1 | 4/2012 | |
| EP | 2628455 A1 | 8/2013 | |
| EP | 3156004 A1 | 4/2017 | |
| EP | 3593742 A1 | 1/2020 | |
| EP | 3669802 A1 | 6/2020 | |
| EP | 3858291 A1 | 8/2021 | |
| ES | 2210456 T3 | 7/2004 | |
| GB | 2427554 A | 1/2007 | |
| GB | 2494820 A | 3/2013 | |
| JP | H0919438 A | 1/1997 | |
| JP | 2014511223 A | 5/2014 | |
| JP | 2014525796 A | 10/2014 | |
| JP | 2015-505250 A | 2/2015 | |
| JP | 2016-513505 A | 5/2016 | |
| JP | 2019-526365 A | 9/2019 | |
| WO | 9424926 A1 | 11/1994 | |
| WO | 9727808 A1 | 8/1997 | |
| WO | 9738631 A1 | 10/1997 | |
| WO | 9920335 A1 | 4/1999 | |
| WO | 9956801 A2 | 11/1999 | |
| WO | 9960933 A1 | 12/1999 | |
| WO | 0121077 A1 | 3/2001 | |
| WO | 0202162 A2 | 1/2002 | |
| WO | 0211627 A2 | 2/2002 | |
| WO | 0243616 A2 | 6/2002 | |
| WO | 02070061 A1 | 9/2002 | |
| WO | 02094111 A2 | 11/2002 | |
| WO | 03002006 A1 | 1/2003 | |
| WO | 03030751 A1 | 4/2003 | |
| WO | 03051448 A2 | 6/2003 | |
| WO | 2004028571 A2 | 4/2004 | |
| WO | 2004056275 A1 | 7/2004 | |
| WO | 2005000130 A1 | 1/2005 | |
| WO | 2005027779 A2 | 3/2005 | |
| WO | 2006021407 A2 | 3/2006 | |
| WO | 2006031410 A2 | 3/2006 | |
| WO | 2006107641 A2 | 10/2006 | |
| WO | 2006135823 A2 | 12/2006 | |
| WO | 2007054307 A2 | 5/2007 | |
| WO | 2007068424 A2 | 6/2007 | |
| WO | 2008034615 A2 | 3/2008 | |
| WO | 2008051431 A1 | 5/2008 | |
| WO | 2008131116 A1 | 10/2008 | |
| WO | 2008135823 A1 | 11/2008 | |
| WO | 2009031338 A1 | 3/2009 | |
| WO | 2009076482 A1 | 6/2009 | |
| WO | 2009086482 A1 | 7/2009 | |
| WO | 2009105710 A1 | 8/2009 | |
| WO | 2010010545 A1 | 1/2010 | |
| WO | 2010046897 A1 | 4/2010 | |
| WO | 2010075565 A2 | 7/2010 | |
| WO | 2010102307 A1 | 9/2010 | |
| WO | 2010146581 A1 | 12/2010 | |
| WO | 2011013556 A1 | 2/2011 | |
| WO | 2011066961 A1 | 6/2011 | |
| WO | 2011082319 A1 | 7/2011 | |
| WO | 2011095352 A1 | 8/2011 | |
| WO | 2011106426 A1 | 9/2011 | |
| WO | 2011110316 A1 | 9/2011 | |
| WO | 2011135556 A1 | 11/2011 | |
| WO | 2012052982 A1 | 4/2012 | |
| WO | 2012064726 A1 | 5/2012 | |
| WO | 2012081020 A1 | 6/2012 | |
| WO | 2012110619 A1 | 8/2012 | |
| WO | 2012120490 A2 | 9/2012 | |
| WO | 2012156924 A1 | 11/2012 | |
| WO | 2013016435 A1 | 1/2013 | |
| WO | 2013072777 A2 | 5/2013 | |
| WO | 2013105099 A2 | 7/2013 | |
| WO | 2013109756 A2 | 7/2013 | |
| WO | 2013187927 A1 | 12/2013 | |
| WO | 2014047650 A1 | 3/2014 | |
| WO | 2014081892 A1 | 5/2014 | |
| WO | 2014139845 A1 | 9/2014 | |
| WO | 2014169266 A1 | 10/2014 | |
| WO | 2014178198 A1 | 11/2014 | |
| WO | 2015061365 A1 | 4/2015 | |
| WO | 2015103547 A1 | 7/2015 | |
| WO | 2015134625 A1 | 9/2015 | |
| WO | 2015179324 A1 | 11/2015 | |
| WO | 2015189354 A1 | 12/2015 | |
| WO | 2016010995 A1 | 1/2016 | |
| WO | 2016089451 A1 | 6/2016 | |
| WO | 2017089424 A1 | 6/2017 | |
| WO | WO 2017/090473 A1 | 6/2017 | |
| WO | WO 2017/103686 A2 | 6/2017 | |
| WO | WO 2017/161204 A1 | 9/2017 | |
| WO | WO 2020/039082 A1 | 2/2020 | |
| WO | WO 2021/113302 A1 | 6/2021 | |

\* cited by examiner

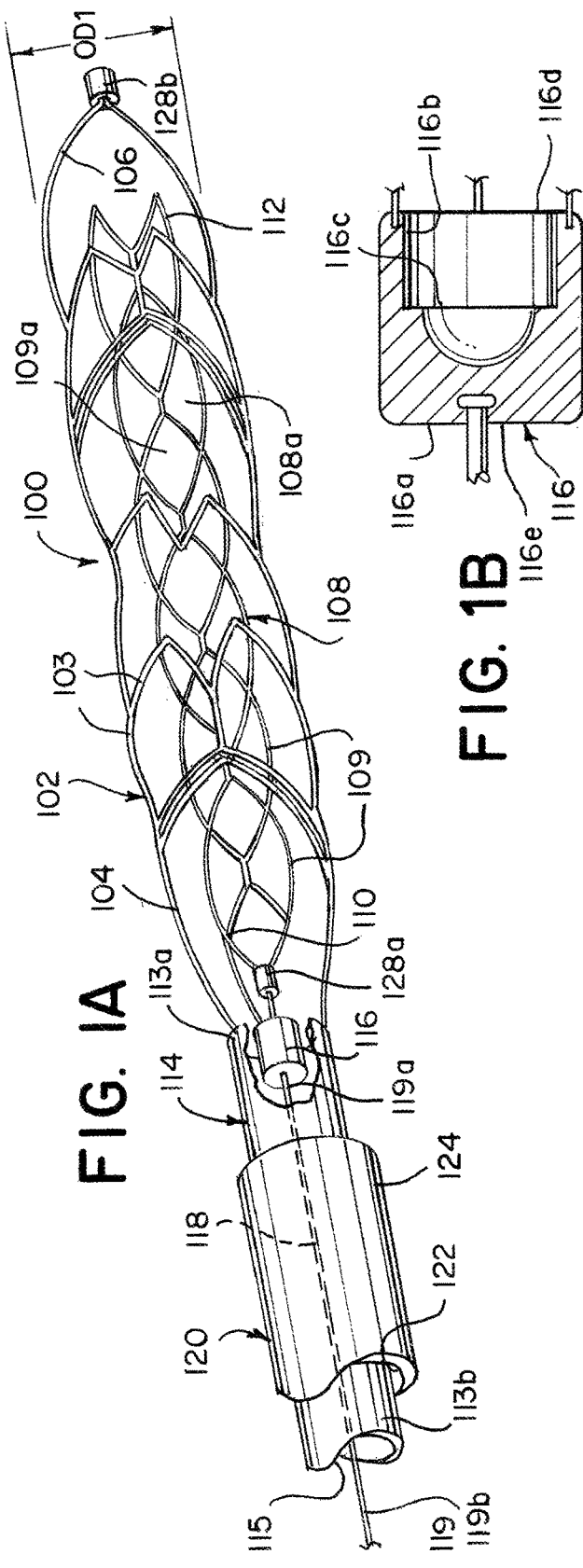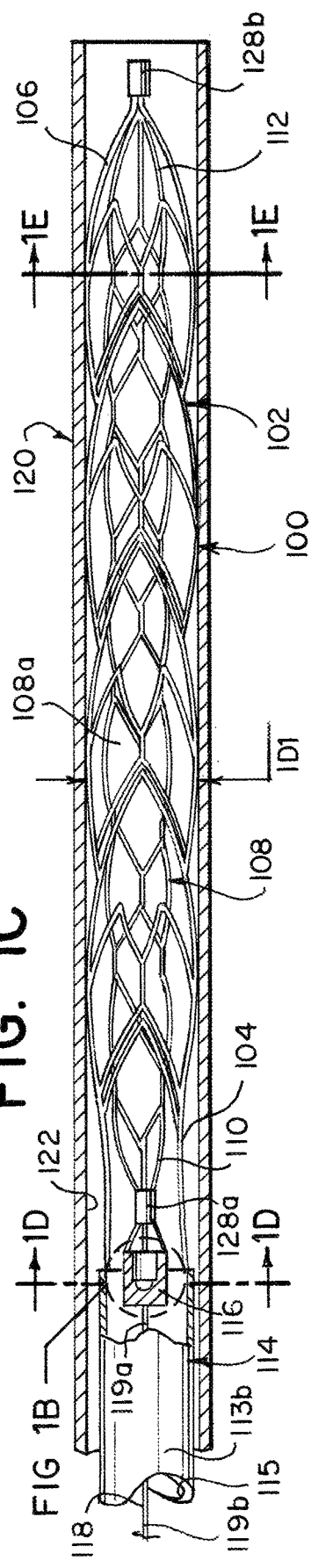

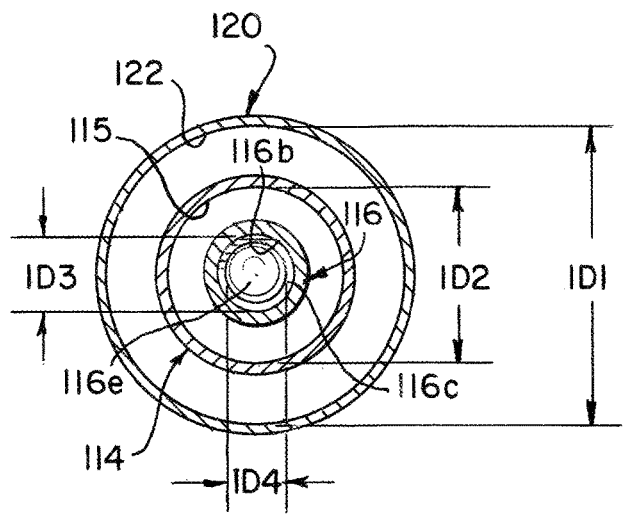
FIG. 1D
FIG. 1E
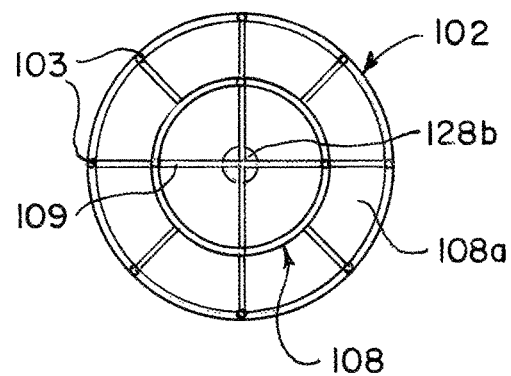
FIG. 1F
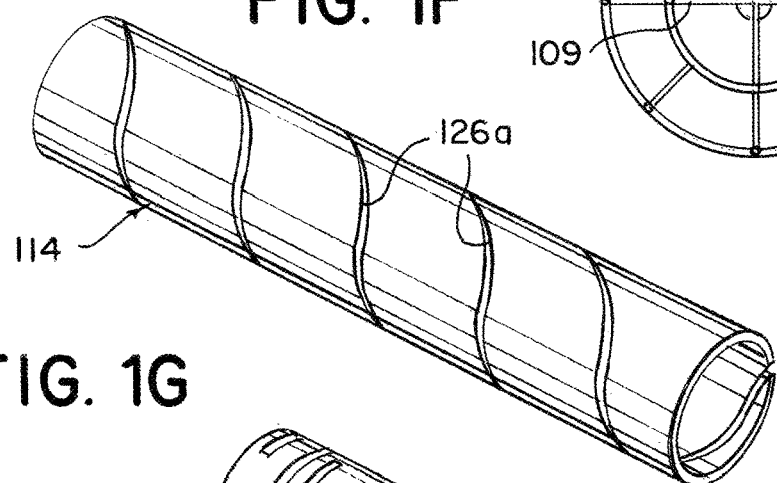
FIG. 1G
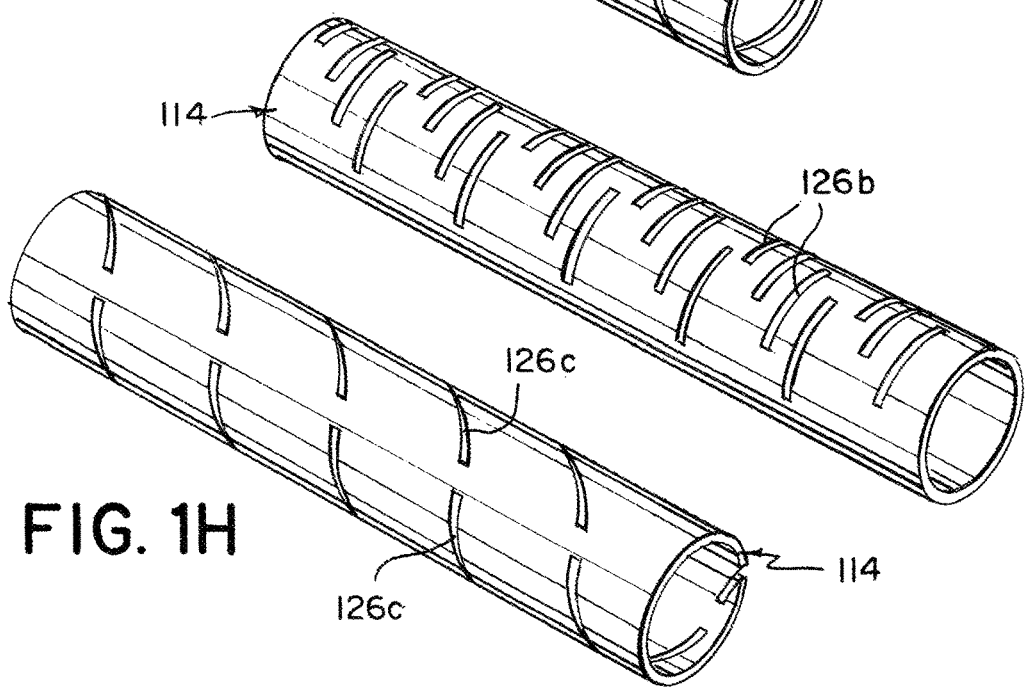
FIG. 1H

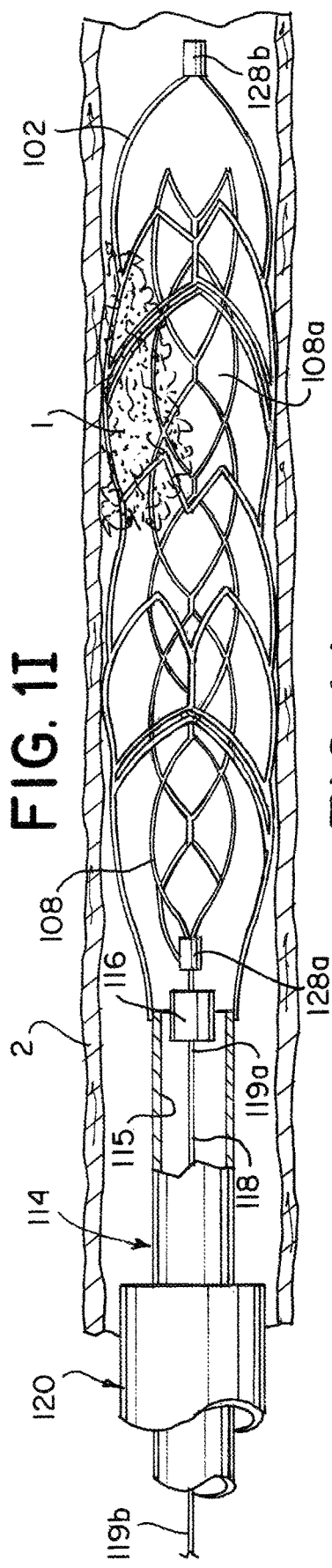
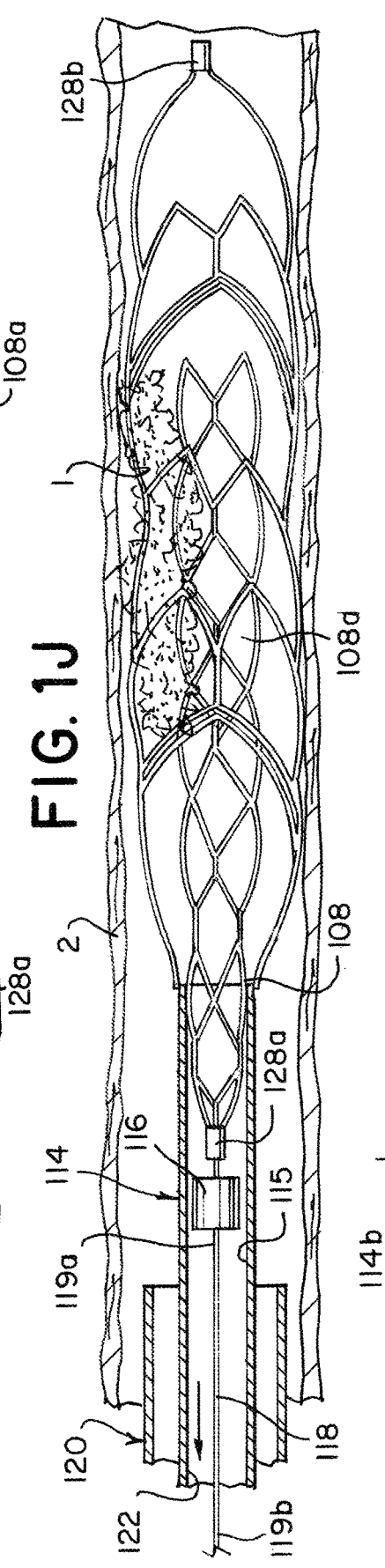
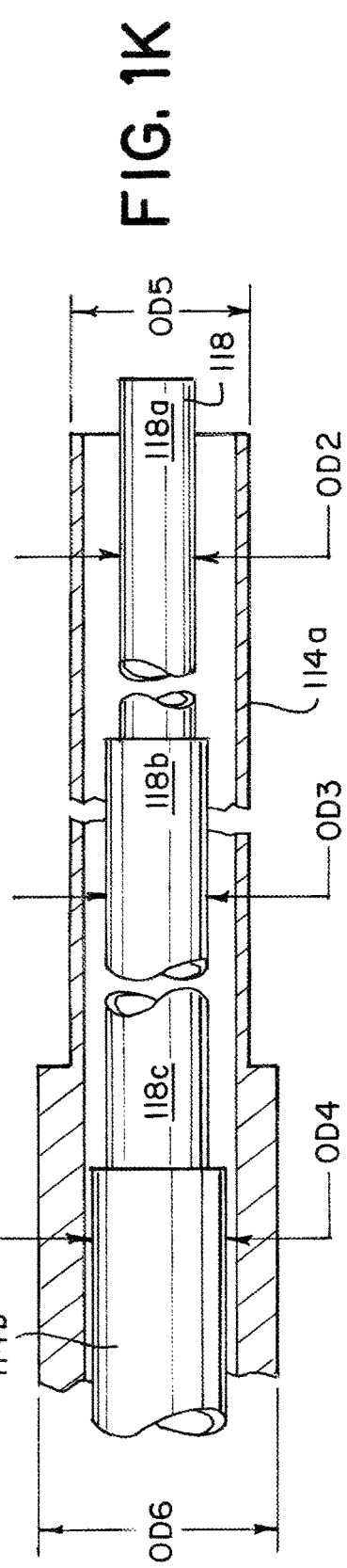

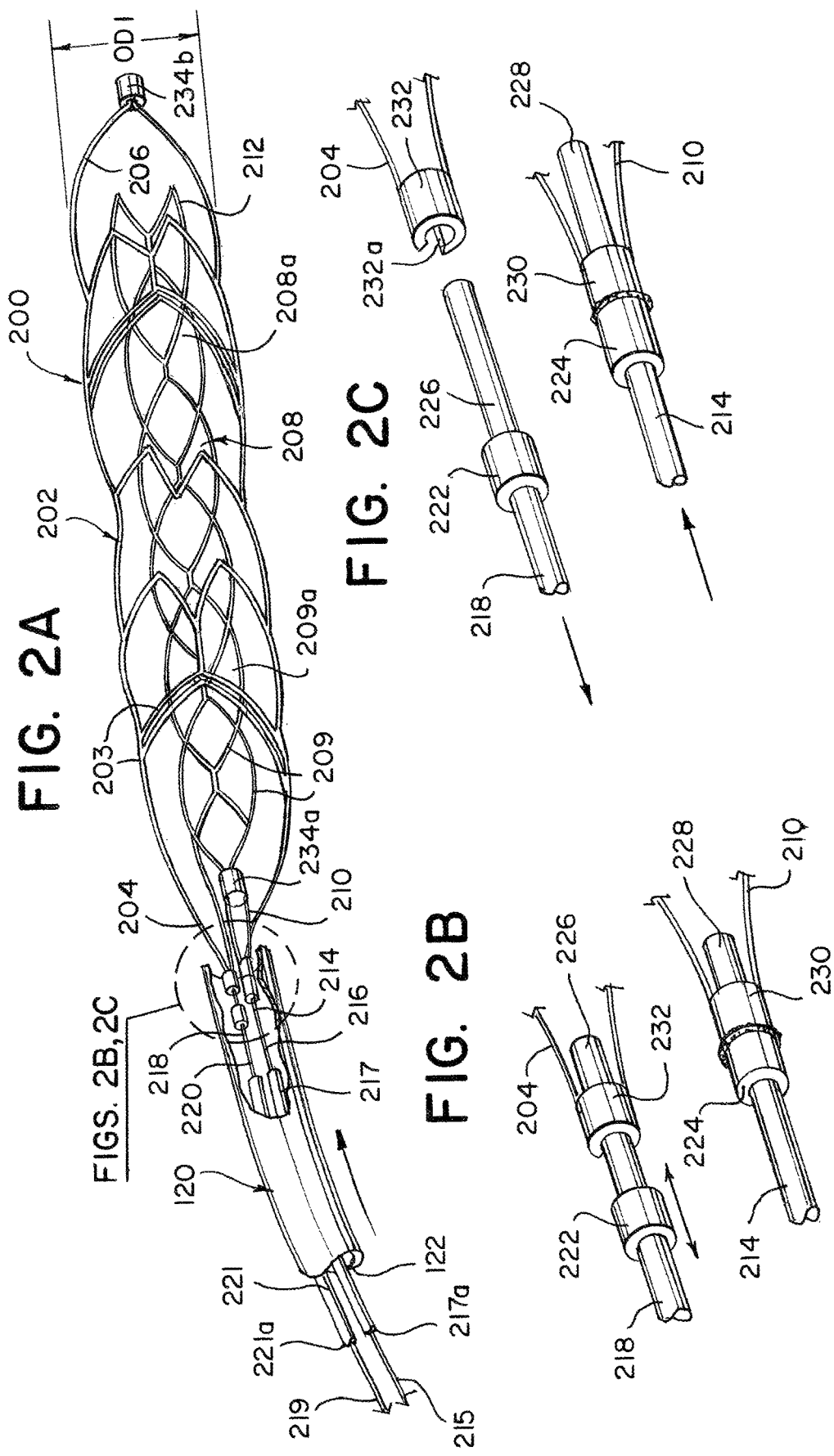

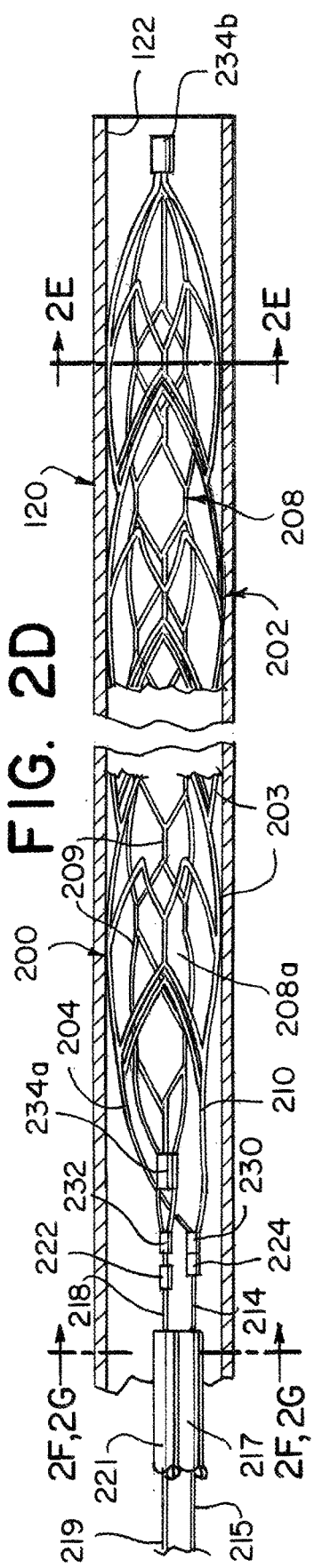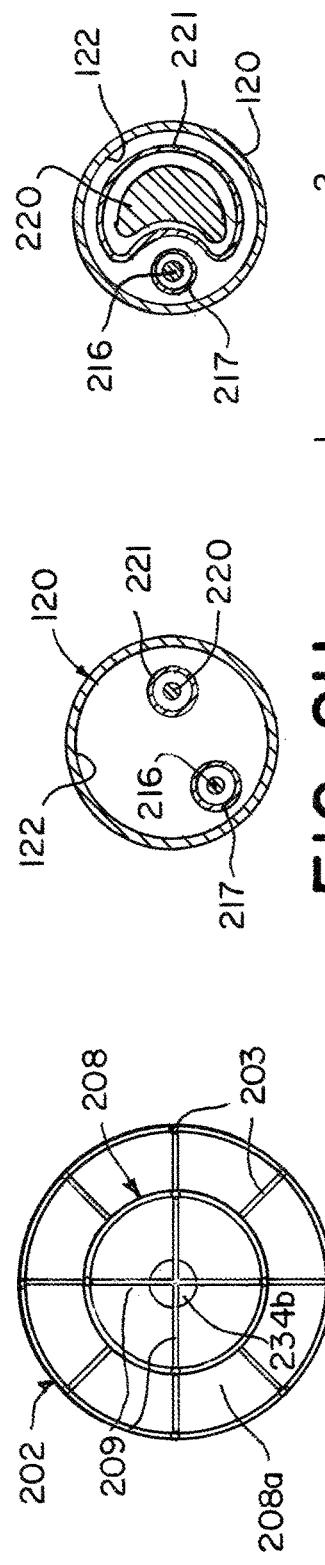

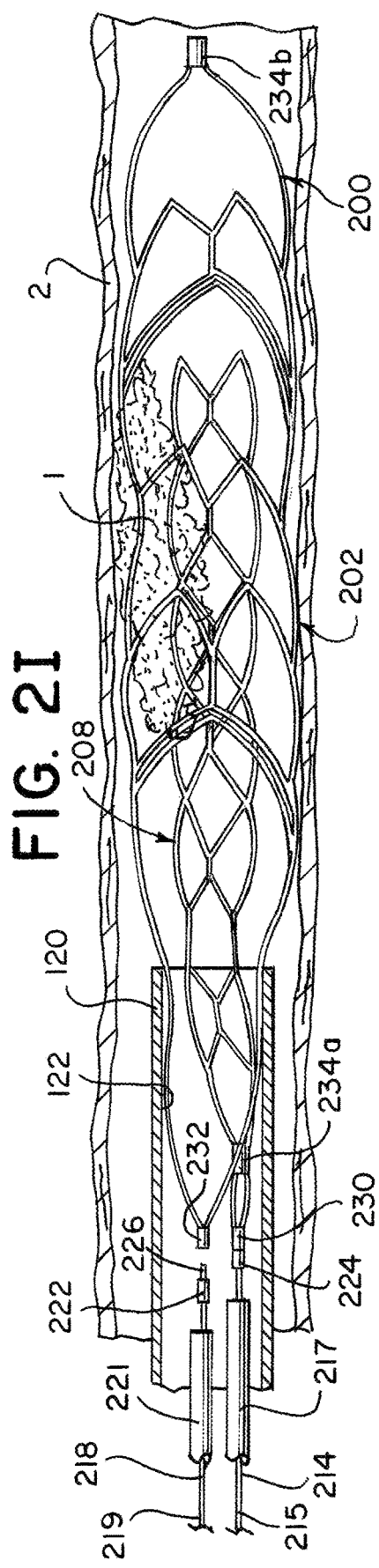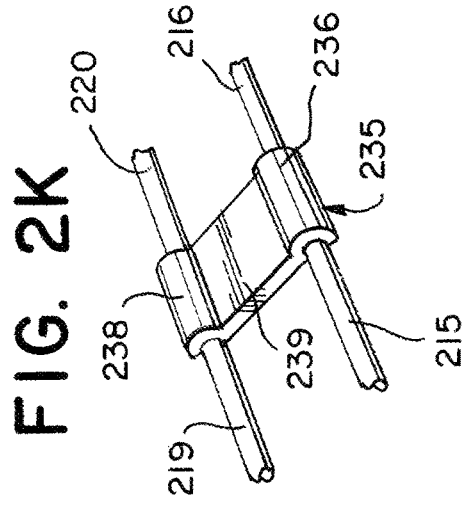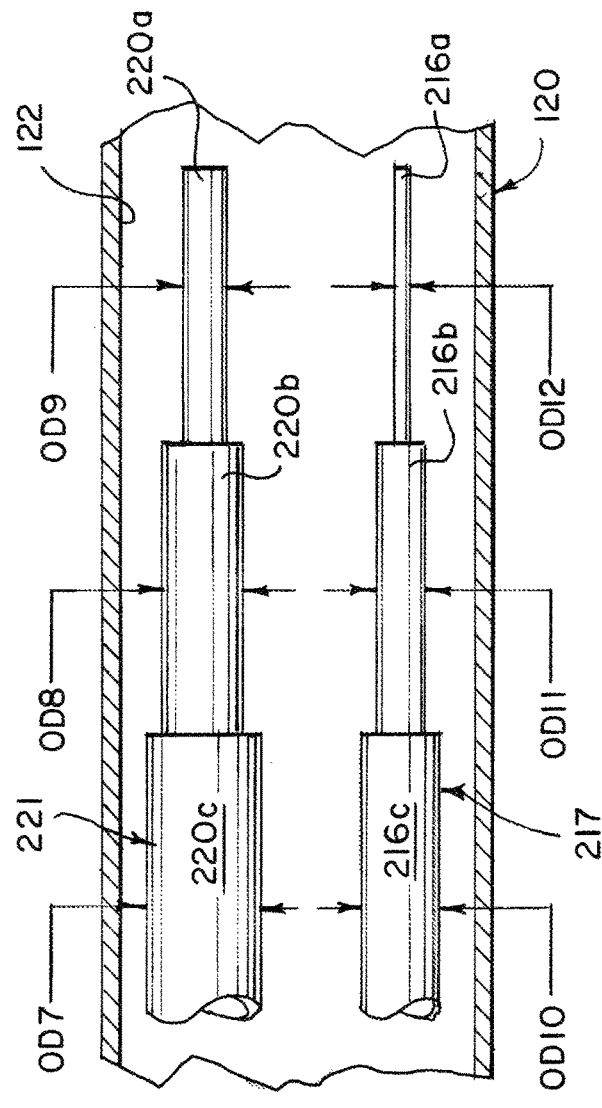

SYSTEMS AND METHODS FOR A DUAL ELONGATED MEMBER CLOT RETRIEVAL APPARATUS

FIELD

The present disclosure generally relates to devices and methods for removing blockages from blood vessels during intravascular medical treatments.

BACKGROUND

Clot retrieval devices are used in mechanical thrombectomy for endovascular intervention, often in cases where patients are suffering from conditions such as acute ischemic stroke (AIS), myocardial infarction (MI), and pulmonary embolism (PE). Acute obstructions may include clot, misplaced devices, migrated devices, large emboli, and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. There are significant challenges associated with designing clot removal devices that can deliver high levels of performance. First, there are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty.

The tortuosity challenge is even more severe in the arteries approaching the brain. For example it is not unusual at the distal end of the internal carotid artery that the device will have to navigate a vessel segment with a 180° bend, a 90° bend and a 360° bend in quick succession over a few centimeters of vessel. In the case of pulmonary embolisms, access is through the venous system and then through the right atrium and ventricle of the heart. The right ventricular outflow tract and pulmonary arteries are delicate vessels that can easily be damaged by inflexible or high-profile devices. For these reasons it is desirable that the clot retrieval device be compatible with as low profile and flexible a guide catheter as possible.

Second, the vasculature in the area in which the clot may be lodged is often fragile and delicate. For example neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Third, the clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore, the inventors have discovered that the properties of the clot may be significantly changed by the action of the devices interacting with it. In particular, compression of a blood clot causes dehydration of the clot and results in a dramatic increase in both clot stiffness and coefficient of friction.

The challenges described above need to be overcome for any devices to provide a high level of success in removing clot and restoring flow. Existing devices do not adequately address these challenges, particularly those challenges associated with vessel trauma and clot properties.

SUMMARY

It is an object of the present design to provide devices and methods to meet the above-stated needs. It is therefore desirable for a clot retrieval device to remove clot from cerebral arteries in patients suffering AIS, from coronary native or graft vessels in patients suffering from MI, and from pulmonary arteries in patients suffering from PE and from other peripheral arterial and venous vessels in which clot is causing an occlusion.

In some examples, the device includes pinch features configured for placement proximate an occlusion (e.g., in the mid internal carotid artery (ICA)). The device can be configured to reperfuse a vessel and/or remove a clot that has a fibrin core. In some examples, the fibrin core can be in a mid- or distal-position in the clot surrounded by relatively soft thrombus.

In some examples, the device can be configured to remove a clot in the M1 bifurcation.

In some examples, the device can be configured to remove a clot in the M2 bifurcation.

In some examples, a method for manufacturing a clot retrieval device can comprise the steps of: patterning a first predetermined pattern on a first tube to form an outer cage, the outer cage comprising an outer diameter, patterning a second predetermined pattern on a second tube to form an inner cage comprising an inner flow channel, and positioning the inner cage concentrically within the outer cage. Additionally, the clot retrieval device can comprise an expanded configuration with a diameter greater than an inner diameter of a microcatheter.

In some examples, an outer diameter of the first tube can approximately equal to the outer diameter of the clot retrieval device in an expanded configuration, thereby expanding an outer cage to a greater diameter under, around, about, or the like a clot or to improve vessel wall apposition when compared to an outer cage of a smaller diameter shapeset to attain the outer diameter of the clot retrieval device, when both clot retrieval devices have equal radial force.

In some examples, an outer diameter of the first tube can be greater than the outer diameter of the clot retrieval device in an expanded configuration, thereby expanding an outer cage to a greater diameter under, around, about, or the like a clot or to improve vessel wall apposition when compared to an outer cage of a smaller diameter shapeset to attain the outer diameter of the clot retrieval device, when both clot retrieval devices have equal radial force.

In some examples, the outer cage can be patterned such that it comprises a ring of eight struts.

In some examples, the inner cage can be patterned such that it comprises a ring of four struts configured to pinch a portion of a clot.

In some examples, the method can further comprise the steps of attaching a first radiopaque marker at a distal end of the outer cage and attaching a second radiopaque marker at a proximal end of the outer cage.

In some examples, the method can further comprise the steps of attaching a first elongated member to a proximal end of the outer cage, the first elongated member configured to move the outer cage between delivery and expanded configurations, and attaching a second elongated member to a proximal end of the inner cage, the second elongated member configured to move the inner cage between delivery and expanded configurations.

In some examples, the second elongated member can be a wire.

In some examples, the first elongated member can be a tube.

In some examples, the first elongated member can comprise a first plurality of segments such that each segment of the plurality comprising decreasing respective outer diameters such that a taper can be formed and the first elongated member can comprise a variable stiffness profile therealong, a proximal end of the first elongated member being stiffer than a distal end of the first elongated member.

In some examples, the second elongated member can be comprise a first plurality of segments such that each segment of the plurality comprising decreasing respective outer diameters such that a taper can be formed and the second elongated member can comprise a variable stiffness profile therealong, a proximal end of the second elongated member being stiffer than a distal end of the second elongated member.

In some examples, the method can further comprise attaching the second elongated member comprising, attaching a distal end of the second elongated member to a proximal end of a receptacle, attaching the proximal end of the inner cage within a cavity of the receptacle, and wherein the second elongated member can be slidable within a lumen of the first elongated member.

In some examples, the receptacle can further comprise a step within the cavity to mitigate over insertion of a proximal end of the inner cage.

In some examples, the method can further comprise the steps of patterning a third pre-determined pattern on the first elongated member to achieve a desired stiffness profile along the first elongated member.

In some examples, the third pre-determined pattern can comprise one or more of a spiral pattern, one or more interrupted spiral patterns, or one or more radial cut patterns.

In some examples, the first and second elongated member can be within separate lumens within the microcatheter.

In some examples, the method can further comprise the steps of uncoupling the first and second elongated members, and forwarding, proximally, the microcatheter over the inner cage causing cells of the inner cage to collapse on the clot exerting additional pressure on that portion of the clot or by causing the clot to become engaged between the distal end of the microcatheter and a cell of the inner cage.

In some examples, the method can further comprise the steps of coupling, using a clip comprising c-shaped features, the first and second elongated members by: attaching, using the c-shaped features, the proximal end of the first and second elongated members respectively, and sliding, distally or proximally, the first and second elongated member in unison.

In some examples, a method for removing a clot can comprise the steps of: locating a microcatheter proximate a clot within a vessel wall, retracting the microcatheter in a proximal direction such that an outer cage and an inner cage within a lumen of the microcatheter expand to about the vessel wall and engage with a portion of the clot, retracting, in a proximal direction, a first elongated member in communication with the inner cage or a second elongated member in communication with the outer cage, such that distance between adjacent struts of the inner cage or struts of the outer cage is reduced exerting pressure on the portion of the clot engaged with inner struts or outer struts, thereby pinching the clot, and forwarding, in a distal direction, the microcatheter over one of the first or a second elongated member. Additionally, forwarding the microcatheter pinches a portion of the clot by causing cells of the inner cage to collapse on the clot exerting additional pressure on that portion of the clot or by causing the clot to become engaged between the distal end of the microcatheter and a cell of the inner cage.

In some examples, the method can further comprise retracting the microcatheter, the first and second elongated members, the inner and outer cage, and the clot from the vessel wall.

In some examples, the outer cage can be patterned such that it comprises a ring of eight struts.

In some examples, the inner cage can be patterned such that it comprises a ring of four struts configured to pinch a portion of the clot.

In some examples, locating the microcatheter proximate the clot can further comprise: coupling, using a clip comprising c-shaped features, the first and second elongated members by: attaching, using the c-shaped features, a proximal end of the first and second elongated members respectively, and sliding the microcatheter and the first and second elongated member in unison towards and proximate to the clot.

In some examples, retracting the first elongated member in communication with the inner cage can further comprise: uncoupling the first and second elongated members from one another such that the first elongated member can be retracted independently of the second elongated member.

In some examples, the second elongated member can be a tube.

In some examples, the first elongated member can be a wire.

In some examples, the first and second elongated members can be within separate lumens of first and second jackets within the microcatheter.

In some examples, the first elongated member can comprise a first plurality of segments such that each segment of the plurality comprising decreasing respective outer diameters such that a taper can be formed and the first elongated member can comprise a variable stiffness profile therealong, a proximal end of the first elongated member being stiffer than a distal end of the first elongated member.

In some examples, the second elongated member comprises a first plurality of segments such that each segment of the plurality comprising decreasing respective outer diameters such that a taper can be formed and the second elongated member can comprise a variable stiffness profile therealong, a proximal end of the second elongated member being stiffer than a distal end of the second elongated member.

In some examples, retracting the first elongated member in communication with the inner cage can further comprise: sliding, in a proximal or distal direction, the first elongated member within a lumen of the second elongated member.

In some examples, a third pre-determined pattern can be patterned on the second elongated member to achieve a desired stiffness profile along the second elongated member.

In some examples, the third pre-determined pattern can comprise one or more of a spiral pattern, one or more interrupted spiral patterns, or one or more radial cut patterns.

In some examples, clot retrieval device can comprise an outer cage, an inner cage concentrically positioned within the outer cage, a first elongated member in communication with the outer cage, and a second elongated member in communication with the inner cage.

In some examples, an outer diameter of the outer cage can be approximately equal to the outer diameter of the clot retrieval device in an expanded configuration, thereby expanding an outer cage to a greater diameter under, around, about, or the like a clot or to improve vessel wall apposition when compared to an outer cage of a smaller diameter shape set to attain the outer diameter of the clot retrieval device, when both clot retrieval devices have equal radial force.

In some examples, an outer diameter of the outer cage can be greater than the outer diameter of the clot retrieval device in an expanded configuration, thereby expanding an outer cage to a greater diameter under, around, about, or the like a clot or to improve vessel wall apposition when compared to an outer cage of a smaller diameter shape set to attain the outer diameter of the clot retrieval device, when both clot retrieval devices have equal radial force.

In some examples, the outer cage can be patterned such that it comprises a ring of eight struts.

In some examples, the inner cage can be patterned such that it comprises a ring of four struts configured to pinch a portion of a clot.

In some examples, the device can further comprise a first radiopaque marker at a distal end of the outer cage, and a second radiopaque marker at a proximal end of the outer cage.

In some examples, the device can further comprise a clip comprising c-shaped features at each end of the clip, each feature configured to receive one of: the first elongated member or the second elongated member, the clip configured to couple the first and second elongated member when attached.

In some examples, the device can further comprise the first elongated member attached to a proximal end of the outer cage, the first elongated member configured to move the outer cage between delivery and expanded configurations, and the second elongated member attached to a proximal end of the inner cage, the second elongated member configured to move the inner cage between delivery and expanded configurations.

In some examples, the second elongated member can be a wire.

In some examples, the first elongated member can be a tube.

In some examples, the first elongated member can comprise a first plurality of segments such that each segment of the plurality comprising decreasing respective outer diameters such that a taper can be formed and the first elongated member can comprise a variable stiffness profile therealong, a proximal end of the first elongated member being stiffer than a distal end of the first elongated member.

In some examples, the second elongated member can comprise a first plurality of segments such that each segment of the plurality comprising decreasing respective outer diameters such that a taper can be formed and the second elongated member can comprise a variable stiffness profile therealong, a proximal end of the second elongated member being stiffer than a distal end of the second elongated member.

In some examples, the device can further comprise a distal end of the second elongated member attached to a proximal end of a receptacle, the proximal end of the inner cage attached within a cavity of the receptacle, and wherein the second elongated member can be slidable within a lumen of the first elongated member.

In some examples, the receptacle can further comprise a step within the cavity to reduce over insertion of a proximal end of the inner cage.

In some examples, the device can further comprise a pre-determined pattern on the first elongated member to achieve a desired stiffness profile along the first elongated member.

In some examples, the pre-determined pattern can comprise one or more of a spiral pattern, one or more interrupted spiral patterns, or one or more radial cut patterns.

In some examples, the first and second elongated member are within respective lumens of a first and second lubricated elongated member jackets within a microcatheter.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

FIG. 1A illustrated an example clot retrieval device in an expanded configuration.

FIG. 1B illustrates a cross-section of an example receptacle.

FIG. 1C illustrates an example clot retrieval device in a delivery configuration.

FIG. 1D illustrates a plan view of an example receptacle.

FIG. 1E illustrates a plan view of an example clot retrieval device.

FIGS. 1F-1H illustrate example predetermined patterns disposed on an elongated member.

FIG. 1I illustrates an example clot retrieval device in a deployed configuration within a vessel and proximate a clot.

FIG. 1J illustrates an example clot retrieval device in a pinched configuration within the vessel and in communication with the clot.

FIG. 1K illustrates a cut view of an example clot retrieval device.

FIGS. 2A-2C illustrates an example clot retrieval device in an expanded configuration.

FIG. 2D illustrates an example clot retrieval device in a delivery configuration.

FIG. 2E illustrates an example cross-section of an example clot retrieval device.

FIGS. 2F-2G illustrate example cross-sections of an example clot retrieval device.

FIG. 2H illustrates an example clot retrieval device in a deployed configuration within a vessel and proximate a clot.

FIG. 2I illustrates an example clot retrieval device in a pinched configuration within the vessel and in communication with the clot.

FIG. 2J illustrates a cut view of an example clot retrieval device.

FIG. 2K illustrates an example clip of an example clot retrieval device.

DETAILED DESCRIPTION

Figure 3:
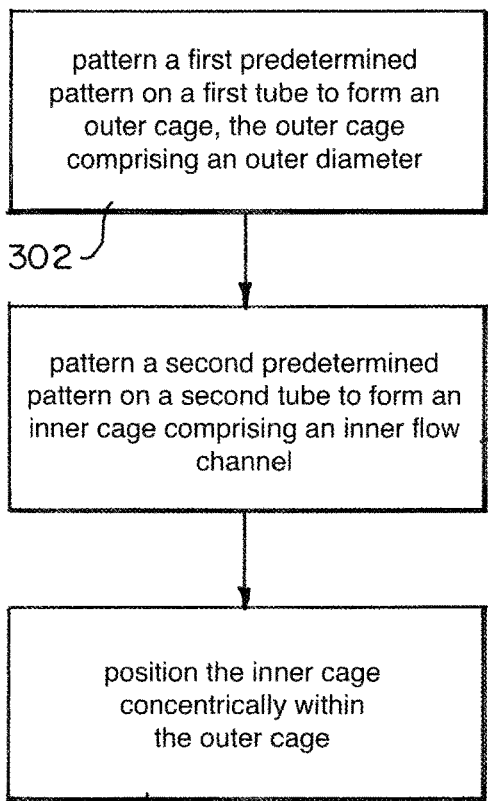
FIG. 3 is a flowchart depicting an assembly of an example clot retrieval device.

Specific examples of the present disclosure are now described in detail with reference to the Figures, where identical reference numbers indicate elements which are functionally similar or identical. The examples address many of the deficiencies associated with traditional catheters, such as inefficient clot removal and inaccurate deployment of catheters to a target site.

Accessing the various vessels within the vascular, whether they are coronary, pulmonary, or cerebral, involves well-known procedural steps and the use of a number of conventional, commercially available accessory products. These products, such as angiographic materials and guidewires are widely used in laboratory and medical procedures. When these products are employed in conjunction with the system and methods of this disclosure in the description below, their function and exact constitution are not described in detail.

The following detailed description is merely exemplary in nature and is not intended to limit the disclosure or the application and uses of the disclosure. Although the description of the disclosure is in many cases in the context of treatment of intracranial arteries, the disclosure may also be used in other body passageways as previously described.

It will be apparent from the foregoing description that, while particular examples of the present disclosure have been illustrated and described, various modifications can be made without departing from the spirit and scope of the disclosure. For example, while the examples described herein refer to particular features, the disclosure includes examples having different combinations of features. The disclosure also includes examples that do not include all of the specific features described. Specific examples of the present disclosure are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in catheter lab procedures. It is assumed in the descriptions below that these products and methods are employed in conjunction with the device and methods of this disclosure and do not need to be described in detail.

The following detailed description is merely exemplary in nature and is not intended to limit the disclosure or the application and uses of the disclosure. Although the description of the disclosure is in many cases in the context of treatment of intracranial arteries, the disclosure may also be used in other body passageways as previously described.

A common theme across many of the disclosed designs is a multi-layer construction in which the device in certain instances can include an outer cage within which, at times, can include an inner cage, both cages being directly or indirectly connected to one or more elongated members. FIG. 1A depicts an example clot retrieval device 100 in an expanded configuration including a first position. The device 100 can include an outer cage 102, an inner cage 108, a receptacle 116, a first elongated member 114, a second elongated member 118, and a microcatheter 120. The microcatheter 120 can include a lumen 122 including an inner diameter ID1. The inner diameter ID1 can be approximately 0.021 inches. Alternatively, the inner diameter ID1 can be approximately 0.5 mm.

Additionally, the device 100 can include a proximal radiopaque band 128a and/or a distal radiopaque band 128b. In the expanded configuration, the outer cage 102 can expand to an outer diameter OD1 and can be outside the lumen 122 of the microcatheter 120. The outer diameter OD1 can be approximately 0.6 mm, 2 mm, 4 mm, or 6.5 mm. Alternatively, the outer diameter OD1 can be between approximately 0.6 mm and 6.5 mm. Alternatively, the outer diameter OD1 can be between approximately 2 mm and 6.5 mm. Alternatively, the outer diameter OD1 can be proportional to an inner diameter ID1 of the microcatheter 120. As an example, the outer diameter OD1 can be two times greater than the inner diameter ID1, for example, an inner diameter ID1 of approximately 0.5 mm would result in an outer diameter OD1 of approximately 1 mm. In this manner, the outer diameter OD1 can be approximately 1 times greater, 4 times greater, 8 times greater, or 13 times greater than the inner diameter ID1. Alternatively, the outer diameter OD1 can be between approximately 4 to 13 times greater than the inner diameter ID1. Additionally, in the expanded configuration, the inner cage 108 can be outside the lumen 122 of the microcatheter 120.

The outer cage 102 can include a proximal end 104, a distal end 106, and an outer diameter OD1. The outer cage 102 can be made of a network of outer struts 103. The proximal end 104 of the outer cage 102 can be configured to attach to a distal end 113a of the first elongated member 114. In the expanded configuration, the proximal end 104 of the outer cage 102 can be distal of a distal end 124 of the microcatheter 120. In a delivery configuration, as described in detail below, the distal end 106 of the outer cage 102 can be proximal of the distal end 124 of the microcatheter 120. The outer cage 102 can transition between the expanded configuration and the delivery configuration by sliding a lumen 122 of the microcatheter 120 in a proximal or distal direction over the outer cage 102, thereby causing the outer cage 102 to expand to the outer diameter OD1, and the inner cage to expand as well. Additionally or alternatively, the network of outer struts 103 of the outer cage 102 can include a pre-determined pattern disposed thereon including eight struts radially distributed, uniformly or non-uniformly, forming a ring-like pattern as discussed in detail below. However, greater or fewer struts can be included as needed or required.

The outer cage 102 can be desirably made from a biocompatible material capable of recovering its shape automatically once released from a highly strained delivery configuration. By way example and without limitation, the outer cage 102 with an outer diameter OD1 of approximately 6.5 mm is collapsed radially to be inserted within the lumen 122 of the microcatheter 120 including, for example, an inner diameter ID1 of approximately 0.5 mm, the outer cage 102 would experience a compressive strain of approximately 92%. As another example, the outer cage 102 with an outer diameter OD1 of approximately 2 mm is collapsed radially to be inserted within the lumen 122 of the microcatheter 120 including, for example, an inner diameter ID1 of approximately 0.5 mm, the outer cage 102 would experience a compressive strain of approximately 75%. Thus, "a highly strained delivery configuration" as that term is used in this disclosure, can be one where the outer cage 102 experiences a compressive strain between approximately 75% and 92%. However, other ranges that correspond to a highly strained configuration are contemplated as needed or required.

In some examples, a superelastic material memory alloy such as Nitinol, or a biocompatible alloy of similar properties. can be particularly suitable. The material could be in many forms such as wire or strip or sheet or tube. A particularly suitable manufacturing process is to laser cut a Nitinol tube and then heat set and electropolish the resultant structure to create a network of struts and connecting elements. This network can be any of huge range of shapes as disclosed herein and may be rendered visible under fluoroscopy through the addition of alloying elements (e.g., Platinum, tantalum, etc.) or through a variety of other coatings or marker bands.

The inner cage 108 can include a proximal end 110, a distal end 112, and a network of inner struts 109. The inner cage 108 can be substantially tubular and concentrically positioned within the outer cage 102 to form a flow channel 108a. The flow channel 108a can be configured to permit fluid flow between the proximal end 104 and the distal end 106 of the outer cage 102. Additionally or alternatively, the flow channel 108a can be configured to permit fluid flow between the proximal end 110 and the distal end 112 of the inner cage 108. Additionally or alternatively, the network of inner struts 109 of the inner cage 108 can include a pre-determined pattern disposed thereon including four struts which can be uniformly or non-uniformly distributed radially to form a ring-like pattern as discussed below. However, greater or fewer struts can be included as needed or required.

Two or more inner struts in the network of inner struts 109 in communication, either directly or indirectly, with one another can be configured to form a pinching cell 109a (e.g., a cell). The network of inner struts 109 can be configured to tweeze a portion of a clot as discussed below in detail. As discussed herein, the term "tweeze" or "tweezing" is intended to refer to the sheathing of the pinching cells that causes respective struts to come together and tweeze or grip at least a portion of clot. In this respect, while the numbers of struts in a respective cell need not be limited, at least two strut surfaces must be included so as to tweeze corresponding clot material. The inner cage 108 can be desirably made from a material capable of recovering its shape automatically once released from a highly strained delivery configuration. A superelastic material memory alloy, such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure to create a network of struts and connecting elements. This network can be any of huge range of shapes as disclosed herein and may be rendered visible under fluoroscopy through the addition of alloying elements (e.g., Platinum, tantalum etc.) or through a variety of other coatings or marker bands.

Turning to FIG. 1B, the receptacle 116 can include a proximal end 116a including an attachment face 116e, a cavity 116b including and opening 116d, and a step 116c located within the cavity 116b and having an inner diameter ID3. The cavity 116b can be configured to receive the proximal end 110 of the inner cage 108. The proximal end 110 of the inner cage 108 can be attached to the cavity 116b of the receptacle 116. Alternatively, the proximal end 110 of the inner cage 108 can be attached to the step 116c of the receptacle 116. The proximal end 110 of the inner cage 108 can be attached using one or more welds. The step 116c can prevent over-insertion of the proximal end 110 of the inner cage 108. The receptacle can be substantially tubular and 116 can be constructed of memory alloy, such as Nitinol, or another biocompatible metal. Additionally or alternatively, the attachment face 116e can be configured to attach to the distal end 119a of the second elongated member 118.

Turning back to FIG. 1A, the first elongated member 114 can include a distal end 113a, a proximal end 113b, and a lumen 115. The distal end 113a of the first elongated member 114 can be attached to the proximal end 104 of the outer cage 102 and configured to move the outer cage 102. The proximal end 104 of the outer cage 102 can be attached using one or more welds. The first elongated member 114 can be constructed from nitinol or another shape-memory alloy. The first elongated member 114 can have one or more pre-determined patterns, for example, one or more of a spiral pattern, one or more interrupted spiral patterns, or one or more radial cut patterns, disposed thereon to provide a variable stiffness profile therealong as discussed below. Additionally or alternatively, the first elongated member 114 can be substantially tubular, and can configured to slide in a distal or proximal direction within the lumen 122 of the microcatheter 120. Additionally or alternatively, the first elongated member 114 can be configured to cause the second elongated member 118 and the receptacle 116, to slide in a distal or proximal direction within the lumen 115 of the first elongated member 114. Additionally or alternatively, the first elongated member 114 can include a taper to provide a variable stiffness profile therealong as discussed in detail below. The first elongated member 114 can be desirably made from a material capable of recovering its shape automatically once released from a highly strained delivery configuration. A superelastic material memory alloy, such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure. This structure can be any of huge range of shapes as disclosed herein and can be rendered visible under fluoroscopy through the addition of alloying elements or through a variety of other coatings or marker bands.

The second elongated member 118 can include a distal end 119a and a proximal end 119b. The distal end 119b of the second elongated member 118 can be configured to attach to the proximal end 116a of the receptacle 116. Additionally or alternatively, the second elongated member can 118 be a wire. Additionally or alternatively, the second elongated member 118 can be a solid shaft and substantially cylindrical. Additionally or alternatively, the second elongated member 118 can be a hollow shaft including a lumen and can be substantially tubular. Additionally or alternatively, the second elongated member 118 can be constructed from nitinol or another shape-memory alloy. Additionally or alternatively, the second elongated member 118 can include a taper to provide a variable stiffness profile therealong as discussed in detail below. The second elongated member 118 can have one or more pre-determined patterns, for example, one or more of a spiral pattern, one or more interrupted spiral patterns, or one or more radial cut patterns, disposed thereon to provide a variable stiffness profile therealong as discussed below.

Additionally or alternatively, the second elongated member 118 can be configured to slide in a distal or proximal direction within the lumen 115 of the first elongated member 114. This can be advantageous as it removes the need to include a PEBAX jacket on the second elongated member 118 and prevents damage to vessels as a result of the "cheese-wire" effect. Additionally or alternatively, the receptacle 116 can be configured to slide in a distal or proximal direction within the lumen 115. The second elongated member 118 can be attached to the receptacle 116 as discussed above, and sliding the second elongated member 118 in a proximal or distal direction can cause the receptacle 116 to slide in a proximal or distal direction within the lumen 115 of the first elongated member 114. Additionally or alternatively, movement of the second elongated member 118 in a distal or proximal direction can cause movement of the inner cage 108 in a distal and/or proximal direction, because, as discussed above, the proximal end 110 of the inner cage 108 can be attached to the receptacle 116, thereby transferring the movement of the second elongated member 118 to the inner cage 108, via receptacle 116. The second elongated member 118 can be desirably made from a material capable of recovering its shape automatically once released from a highly strained delivery configuration. A superelastic material memory alloy such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure. This structure can be any of huge range of shapes as disclosed herein and may be rendered visible under fluoroscopy through the addition of alloying elements or through a variety of other coatings or marker bands.

The microcatheter 120 can include a lumen, 122, and a distal end 124. The inner diameter ID1 of the microcatheter 120 can be dimensioned to slidably position within the lumen 122 at least the first elongated member 114, and the outer cage 102. Additionally, the inner cage 108 can be configured to slide within the lumen 122. The second elongate member 118 can be configured to slide within the lumen 122.

The proximal radiopaque band 128a can be positioned at the proximal end 104 of the outer cage 102. Additionally or alternatively, the proximal radiopaque band 128a can be positioned at the proximal end 110 of the inner cage 108. The proximal radiopaque band 128a can be constructed of platinum or other radiopaque materials. The proximal radiopaque band 128a can be desirably made from a material capable of recovering its shape automatically once released from a highly strained delivery configuration. A superelastic material memory alloy such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure. This structure can be any of huge range of shapes as disclosed herein and may be rendered visible under fluoroscopy through the addition of alloying or through a variety of other coatings or marker bands.

The distal radiopaque band 128b can be positioned at the distal end 106 of the outer cage 102. Additionally or alternatively, the distal radiopaque band 128b can be positioned at the distal end 112 of the inner cage 108. The distal radiopaque band 128b can be constructed of platinum or other radiopaque materials. The distal radiopaque band 128b can be desirably made from a material capable of recovering its shape automatically once released from a highly strained delivery configuration. A superelastic material memory alloy such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure to create a structure. This structure can be any of huge range of shapes as disclosed herein and may be rendered visible under fluoroscopy through the addition of alloying elements or through a variety of other coatings or marker bands.

FIG. 1C depicts device 100 in a delivery configuration including a second position. In the delivery configuration, the device 100 can be outside of a patient ready for delivery, and the outer cage 102 can be within the lumen 122 of the microcatheter 120, and can include a diameter substantially similar to the inner diameter ID1 of the microcatheter 120. Alternatively, in the delivery configuration, at least a portion of the device 100 can be within a vessel of the patient. Additionally, in the delivery configuration, the distal end 106 of the outer cage 102 and the distal end 112 of the inner cage 108 can be within the lumen 122 of the microcatheter 120 including an inner diameter ID1. The inner diameter ID1 of the microcatheter 120 can be less than the outer diameter OD1 of the outer cage 102 in the expanded configuration. Additionally, the distal radiopaque band 128b can be within the lumen 122.

FIG. 1D depicts a front plan cross-section of a clot retrieval device 100. This view depicts various aspects of the receptacle 116 in detail. The receptacle 116 can include the opening 116d including an inner diameter ID3. The receptacle 116 can include the cavity 116b including an inner diameter ID3 for at least a portion of the cavity 116b. The receptacle 116 can be positioned within the lumen 115 of the first elongated member 114. The first elongated member 114 can include an inner diameter ID2 including a dimension greater than the inner diameter ID3 of the opening 116d, but less than the inner diameter ID1 of the microcatheter 120. The step 116c can be disposed within the cavity 116b of the receptacle 116. To prevent over-insertion of the proximal end 110 of the inner cage 108, the step 116c reduces the inner diameter ID3 of the cavity 116b, to an inner diameter ID4, thereby preventing the proximal end 110 of the inner cage 108 from being welded to the proximal end 116a of the receptacle 116. The proximal end 110 of the inner cage 108 can be attached to the cavity 116b of the receptacle 116. Alternatively, the proximal end 110 of the inner cage 108 can be attached to the step 116c of the receptacle 116. The proximal end 110 of the inner cage 108 can be attached using one or more welds.

FIG. 1E depicts a cross-section of the outer cage 102 including the network of outer struts 103 and the inner cage 108 including the network of inner struts 109 while in the delivery position. Additionally or alternatively, the network of outer struts 103 can be patterned to include between six and ten struts, which can be uniformly or non-uniformly distributed around a centerline of the outer cage 102. Additionally or alternatively, the network of inner struts 109 can be patterned to include between two and six struts, which can be uniformly or non-uniformly distributed around a centerline of the inner cage 108.

FIG. 1F-1H depict examples for pre-determined patterns disposed on the first elongated member 114. FIG. 1F depicts the first elongated member 114 including a spiral cut 126a disposed thereon. The spiral cut 126a can be a helix having a uniform spacing between each revolution of the helix and/or a uniform helix angle forming the uniform spacing between each revolution of the helix along a length of the first elongated member 114. Alternatively, the spiral cut 126a can be a helix having a non-uniform spacing between each revolution of the helix and/or a non-uniform helix angle forming the non-uniform spacing between each revolution of the helix along a length of the first elongated member 114, thereby resulting in variable stiffness of the first elongated member 114 along the length of the first elongated member 114. Additionally, the second elongate member 118, can include a spiral cut, such as spiral cut 126a, disposed thereon. FIG. 1G depicts the first elongated member 114 including an interrupted spiral pattern 126b disposed thereon. The interrupted spiral pattern 126b can be a helix cut having a uniform spacing between each revolution of the helix and/or a uniform helix angle forming the uniform spacing between each revolution of the helix along a length of the first elongated member 114. Alternatively, the interrupted spiral pattern 126b can be a helix cut including a non-uniform spacing between each revolution of the helix and/or a non-uniform helix angle forming the non-uniform spacing between each revolution of the helix along a length of the first elongated member 114, thereby resulting in variable stiffness of the first elongated member 114 along the length of the first elongated member 114. Additionally, the second elongate member 118, can include an interrupted spiral pattern, such as interrupted spiral pattern 126b, disposed thereon. The helix (or helical) cut need not be a continuous cut, said differently, there can be a plurality of cuts interrupted, or separated, by material of the first elongated member 114. FIG. 1H depicts the first elongated member 114 including a radial cut pattern disposed thereon. The radial pattern 126c can be a plurality of cuts perpendicular to the length of the first elongated member 114 and repeated uniformly along a length of the first elongated member 114. Alternatively, the radial pattern 126c can be a plurality of cuts perpendicular to the length of the first elongated member 114 and repeated non-uniformly along a length of the first elongated member 114. Additionally, the second elongate member 118, can include a radial pattern, such as radial pattern 126c, disposed thereon.

FIG. 1I illustrates an example clot retrieval device 100 in a deployed configuration including a third position within a vessel 2 and in communication with a clot 1. Additionally, in the deployed configuration, the outer cage 102 can be outside (e.g., distal of) the lumen 122 of the microcatheter 120. Additionally, in the deployed configuration, the inner cage 108 can be outside (e.g., distal of) the lumen 122 of the microcatheter 120. The retraction of the microcatheter 120 in a proximal direction can deploy the inner cage 108 and the outer cage 102. As a result, a portion of the clot 1 can be in communication with the outer cage 102 and/or the inner cage 108. Specifically, the portion of the clot 1 can be in communication with the network of inner struts 109 and/or the network of outer struts 103. The flow channel 108a of the inner cage 108 can allow fluid to flow beyond the clot 1. The first and second elongated member 114, 118 can move independently of each other in a proximal and/or distal direction. Additionally or alternatively, the first and second elongated members 114, 118 can be coupled at respective proximal ends 113b, 119b of the first and second elongated members 114, 118 such that they move together in a proximal and/or distal direction.

FIG. 1J illustrates an example clot retrieval device 100 in a pinched configuration within the vessel 2 and in communication with the clot 1. Additionally, in the pinched configuration, a portion of the outer cage 102 can be outside the lumen 122 of the microcatheter 120 and in communication with a portion of the clot 1. Additionally, in the pinched configuration, a portion of the inner cage 108 can be outside the lumen 122 of the microcatheter 120 and pinching, or tweezing, a portion of the clot 1. The first and second elongated member 114, 118 can move independently of each other in a proximal and/or distal direction. Additionally or alternatively, the first and second elongated members 114, 118 can be uncoupled at respective proximal ends 113b, 119b of the first and second elongated members 114, 118 such that they move independently. The microcatheter 120 and/or the first elongated member 114 can be forwarded (e.g., resheathed) over the second elongated member 118. Additionally or alternatively, the microcatheter 120 and/or the first elongated member 114 can be forwarded over the inner cage 108 such that network of inner struts 109, configured to form pinch cells 109a, can pinch a portion of the clot 1. It can be advantageous for the for the first and second elongated member 114, 118 to move independently because the network of outer struts 103 can remain in communication and/or engaged with a portion of the clot 1 while the pinching cells 109a of the inner cage 108 can pinch a portion of the clot 1.

FIG. 1K depicts an example first elongated member 114 and an example second elongated member 118 including a taper. The first elongated member 114 can include a first plurality of segments 114a, 114b such that each segment of the plurality can include increasing respective outer diameters OD5, and OD6 such that the taper can be formed. Additionally or alternatively, increasing corresponding inner diameters of the first plurality of segments 114a, 114b is contemplated. As an example, of outer diameter OD6 of segment 114b is greater than outer diameter OD5 of segment 114a, an inner diameter associated with segment 114b can be greater than an inner diameter associated with segment 114a. The taper can be continuous, for example, and can include an outer diameter at the proximal end 113b of the first elongated member 114 and a smaller outer diameter at the distal end 113a of the first elongated member 114. Additionally or alternatively, a continuous taper for corresponding inner diameters is also contemplated. As an example, the continuous taper for corresponding inner diameters can include an inner diameter at the proximal end 113b of the first elongated member 114 and a smaller inner diameter at the distal end 113a of the first elongated member 114. The first elongated member 114 can include a variable stiffness profile therealong, a proximal end 113b of the first elongated member 114 being stiffer than a distal end 113a of the first elongated member 114. The second elongated member 118 can include a first plurality of segments 118a, 118b, and 118c such that each segment of the plurality can include increasing respective outer diameters OD2, OD3, and OD4 such that the taper can be formed. The taper can be continuous, for example, can include an outer diameter at the proximal end 119b of the second shaft 118 and a smaller outer diameter at the distal end 119a of the second shaft 118. The second elongated member 118 can include a variable stiffness profile therealong, a proximal end 113b of the first elongated member 114 being stiffer than a distal end 113a of the first elongated member 114. Additionally or alternatively, only the second elongated member 118 includes a taper. Additionally or alternatively, only the first elongated member 114 includes a taper. In examples, the first and second elongated members 114, 118 include a taper.

FIGS. 2A-2C illustrates an example clot retrieval device 200 in an expanded configuration including a first position, as that configuration has been previously described. The device 200 can include an outer cage 202, an inner cage 208, a first elongated member 220, a second elongated member 216, a first lubricating jacket 221, a second lubricating jacket 217, and a microcatheter 120. Additionally, the device 200 can include a proximal radiopaque band 134a and/or a distal radiopaque band 134b.

The outer cage 202 can include a proximal end 204, a distal end 206, and an outer diameter OD1. The outer cage 202 can be made of a network of outer struts 203. The proximal end 204 of the outer cage 202 can be configured to attach to a distal end 218 of the first elongated member 220. In the expanded configuration, the proximal end 204 of the outer cage 202 can be distal of the distal end 124 of the microcatheter 120, thereby causing the outer cage 202 to expand to the outer diameter OD1, and the inner cage 208 to expand as well. In a delivery configuration, as described in detail below, the distal end 206 of the outer cage 202 can be proximal of a distal end 124 microcatheter 120. The outer cage 202 can transition between the deployed configuration and the delivery configuration by sliding a lumen 122 of the microcatheter 120 in a proximal or distal direction over the outer cage 202. Additionally or alternatively, the network of outer struts 203 of the outer cage 202 can include a pre-determined pattern disposed thereon including eight struts distributed, uniformly or non-uniformly, radially forming a ring-like pattern as discussed in detail below. However, greater or fewer struts can be included as needed or required. Turning to FIGS. 2B and 2C, a c-shaped collar 232 can be disposed at the proximal end 204 of the outer cage 202. The c-shaped collar 232 can include a lumen 232a configured to receive and be in communication with a positioning pin 226 at a distal end 218 of a first elongated member 220. Additionally, the c-shaped collar 232 can be in communication with the network of outer struts 203. Additionally, the c-shaped collar 232 can abut a step 222 of the first elongated member 220 such that sliding the first elongated member in a distal direction moves the outer cage 202 in the distal direction. Additionally, sliding the first elongated member 220 in a proximal direction disengages the step 222 from the c-shaped collar 232 and slides the positioning pin 226 from the lumen 232a of the c-shaped collar 232 such that the outer cage 202 does not move in the proximal direction.

Turning back to FIG. 2A, the outer cage 202 can be desirably made from a material capable of recovering its shape automatically once released from a highly strained delivery configuration. A superelastic material memory such as Nitinol or a biocompatible metal alloy of similar properties can be particularly suitable. The material could be in many forms such as wire or strip or sheet or tube. A particularly suitable manufacturing process is to laser cut a Nitinol tube and then heat set and electropolish the resultant structure to create a network of struts and connecting elements. This network can be any of huge range of shapes as disclosed herein and may be rendered visible under fluoroscopy through the addition of alloying elements or through a variety of other coatings or marker bands.

The inner cage 208 can include a proximal end 210, a distal end 212, and a network of inner struts 209. The inner cage 208 can be substantially tubular and concentrically positioned within the outer cage 202 to form a flow channel 208a. The flow channel 208a can be configured to permit fluid flow between the proximal end 204 and the distal end 206 of the outer cage 202. Additionally or alternatively, the flow channel 208a can be configured to permit fluid flow between the proximal end 210 and the distal end 212 of the inner cage 208. Additionally or alternatively, the network of inner struts 209 of the inner cage 208 can include a pre-determined pattern disposed thereon including four struts which can be uniformly or non-uniformly distributed radially to form a ring-like pattern as discussed below. However, greater or fewer struts can be included as needed or required. Turning to FIGS. 2B and 2C, a c-shaped collar 230 can be disposed at the proximal end 210 of the inner cage 208. The c-shaped collar 230 can be attached to a guide pin 228 at a distal end 214 of a second elongated member 216. Additionally, the c-shaped collar 230 can be in communication with the network of inner struts 209. Additionally or alternatively, the c-shaped collar 232 can abut a step 224 of the second elongated member 216 such that sliding the second elongated member in a distal or proximal direction moves the inner cage 208 in the respective direction. The c-shaped collar 230 can be welded to the guide pin 228. Additionally or alternatively, the c-shaped collar can be welded to the step 224.

Turning back to FIG. 2A, two or more struts in the network of inner struts 209 can be in communication, either directly or indirectly, with one another can be configured to form a pinching cell 209a (e.g., a cell). The network of inner struts 209 can be configured to tweeze a portion of a clot as discussed below in detail. As discussed herein, the term "tweeze" or "tweezing" is intended to refer to the sheathing of the pinching cells that causes respective struts to come together and tweeze or grip at least a portion of clot. In this respect, while the numbers of struts in a respective cell need not be limited, at least two strut surfaces must be included so as to tweeze corresponding clot material. The inner cage 208 can be desirably made from a material capable of recovering its shape automatically once released from a highly strained delivery configuration. A superelastic material memory alloy such as Nitinol or an alloy of similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of huge range of shapes as disclosed herein and may be rendered visible under fluoroscopy through the addition of alloying elements or through a variety of other coatings or marker bands.

Turning to FIGS. 2B-C, the first elongated member 220 can include a distal end 218 and a proximal end 219. Additionally, at the distal end 218, the first elongated member 220 can include the step 222 configured to abut with the c-shaped collar 232 of the outer cage 202. Additionally, the positioning pin 226 disposed distal of the step 222 can be configured to be inserted within the lumen 232a of the c-shaped collar 232 of the outer cage 202. Turning back to FIG. 2A, the proximal end 218 of the first elongated member 220, can be configured to receive a clip configured to couple the first elongated member 220 with the second elongated member 216, such that proximal or distal sliding of the first elongated member 220 or second elongated member 216 results in a respective sliding of the other elongated member, as discussed below. Additionally or alternatively, the first elongated member 220 can include one or more pre-determined patterns, for example, one or more of a spiral pattern (e.g., spiral cut 126a), one or more interrupted spiral patterns (e.g., interrupted spiral pattern 126b), or one or more radial cut patterns (e.g., radial pattern 126c), disposed thereon to provide a variable stiffness profile therealong as discussed below. Additionally or alternatively, the first elongated member 220 can be a wire, a shaft or a tube, and can configured to slide in a distal or proximal direction within the lumen 122 of the microcatheter 120. The first elongated member 220 can be desirably made from a material capable of recovering its shape automatically once released from a highly strained delivery configuration. A superelastic material memory alloy such as Nitinol or a biocompatible alloy of similar properties is particularly suitable. The material could be in many forms such as wire or strip or sheet or tube. A particularly suitable manufacturing process is to laser cut a Nitinol tube and then heat set and electropolish the resultant structure. This structure can be any of huge range of shapes as disclosed herein and may be rendered visible under fluoroscopy through the addition of alloying elements (e.g., Platinum) or through a variety of other coatings or marker bands.

The first lubricating jacket 221 can include a lumen 221a. The first elongated member 220 can be configured to slide in a proximal or distal direction within the lumen 221a of the first lubricating jacket 221. The lubrication provided by the first lubricating jacket 221 can be advantageous in reducing friction between the first elongated member 220 and, for example, the lumen 221a of the first lubricating jacket 221. Additionally or alternatively, the first lubricating jacket 221 can isolate at least a portion of the first elongated member 220 from rubbing against the lumen 122 of the microcatheter 120 and/or the second lubricating jacket 217. The lubricant can be, for example, an elastomer such as PEBAX and/or other suitable lubricants. The first elongated member 220 and the first lubricating jacket 221 can include a substantially circular or elliptical cross-section. Alternatively, the first elongated member 220 and the first lubricating jacket 221 can include a substantially non-symmetric cross-section. Additionally, the first elongated member 220 can be positioned concentrically within the lumen 221a of the first lubricating jacket 221.

Turning back to FIGS. 2B-C. the second elongated member 216 can include a distal end 214 and a proximal end 215. Additionally, at the distal end 214, the second elongated member 216 can include the step 224 configured to attach to the c-shaped collar 230 of the inner cage 208. Additionally, the guiding pin 228 located distal of the step 224 can be configured to attach the c-shaped collar 230 of the inner cage 208. Turning back to FIG. 2A, the proximal end 215 of the second elongated member 216, can be configured to receive a clip configured to couple the second elongated member 216 with the first elongated member 220, such that proximal or distal sliding of the second elongated member 216 or first elongated member 220 results in a respective sliding of the other elongated member, as discussed below.

Additionally or alternatively, the second elongated member 216 can include one or more pre-determined patterns, for example, one or more of a spiral pattern (e.g., spiral cut 126a), one or more interrupted spiral patterns (e.g., interrupted spiral pattern 126b), or one or more radial cut patterns (e.g., radial pattern 126c), disposed thereon to provide a variable stiffness profile therealong as discussed below. Additionally or alternatively, the second elongated member 216 can be a wire, a shaft or a tube, and can configured to slide in a distal or proximal direction within the lumen 122 of the microcatheter 120. The second elongated member 216 can be desirably made from a material capable of recovering its shape automatically once released from a highly strained delivery configuration. A superelastic material memory alloy such as Nitinol or a biocompatible metal alloy of similar properties is particularly suitable. The material could be in many forms such as wire or strip or sheet or tube. A particularly suitable manufacturing process is to laser cut a Nitinol tube and then can be heat set and electropolish the resultant structure. This structure can be any of huge range of shapes as disclosed herein and may be rendered visible under fluoroscopy through the addition of alloying elements or through a variety of other coatings or marker bands.

The second lubricating jacket 217 can include a lumen 217a. The second elongated member 216 can be configured to side in a proximal or distal direction within the lumen 217a of the second lubricating jacket 217. The lubrication provided by the second lubricating jacket 217 can be advantageous in reducing friction between the second elongated member 216 and, for example, the lumen 217a of the second lubricating jacket 217. Additionally or alternatively, the second lubricating jacket 217 can isolate at least a portion of the second elongated member 216 from rubbing against the lumen 122 of the microcatheter 120 and/or the first lubricating jacket 221. The lubricant can be, for example, an elastomer such as PEBAX and/or other suitable lubricants. The second elongated member 216 and the second lubricating jacket 217 can include a substantially circular or elliptical cross-section. Alternatively, the second elongated member 216 and the second lubricating jacket 217 can include a substantially non-symmetric cross-section. Additionally, the second elongated member 216 can be positioned concentrically within the lumen 217a of the second lubricating jacket 217.

The proximal radiopaque band 234a can be positioned at the proximal end 204 of the outer cage 202. Additionally or alternatively, the proximal radiopaque band 234a can be positioned at the proximal end 210 of the inner cage 208. The proximal radiopaque band 234a can be constructed of platinum or other radiopaque materials. The proximal radiopaque band 234a can be desirably made from a material capable of recovering its shape automatically once released from a highly strained delivery configuration. A superelastic material memory alloy such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure. This structure can be any of huge range of shapes as disclosed herein and may be rendered visible under fluoroscopy through the addition of alloying elements or through a variety of other coatings or marker bands.

The distal radiopaque band 234b can be positioned at the distal end 206 of the outer cage 202. Additionally or alternatively, the distal radiopaque band 234b can be positioned at the distal end 212 of the inner cage 208. The distal radiopaque band 234b can be constructed of platinum or other radiopaque materials. The distal radiopaque band 234b can be desirably made from a material capable of recovering its shape automatically once released from a highly strained delivery configuration. A superelastic material memory alloy such as Nitinol or an alloy of similar properties can be particularly suitable. The material could be in many forms such as wire or strip or sheet or tube. A particularly suitable manufacturing process is to laser cut a Nitinol tube and then heat set and electropolish the resultant structure. This structure can be any of huge range of shapes as disclosed herein and may be rendered visible under fluoroscopy through the addition of alloying elements or through a variety of other coatings or marker bands.

FIG. 2D illustrates the device 200 in a delivery configuration in a second position, as that configuration has been previously described. the distal end 206 of the outer cage 202 and the distal end 212 of the inner cage 208 can be proximate the distal end 124 of the microcatheter 120 and within the lumen 122 of the microcatheter 120 including an inner diameter ID1. Additionally, the distal radiopaque band 128b can be within the lumen 122. The inner diameter ID1 of the microcatheter 120 can be less than the outer diameter OD1 of the outer cage 202 in the expanded configuration. In the delivery configuration, the distal end 206 of the outer cage 2020 can be proximal of a distal end 124 microcatheter 120. The outer cage 202 can transition between the expanded configuration and the delivery configuration by sliding a lumen 122 of the microcatheter 120 in a proximal or distal direction over the outer cage 202.

FIG. 2E depicts a cross-section of the outer cage 202 including the network of outer struts 203 and the inner cage 208 including the network of inner struts 209 while in the delivery position. Additionally or alternatively, the network of outer struts 203 can be patterned to include between six and ten struts, uniformly or non-uniformly distributed, around a centerline of the outer cage 202. Additionally or alternatively, the network of inner struts 209 can be patterned to include between two and six struts, which can be uniformly or non-uniformly distributed around a centerline of the inner cage 208.

FIGS. 2F-2G illustrate example cross-sections of an example clot retrieval device. FIG. 2F illustrates an example configuration of the first and second elongated members 220, 216 within the lumen 122 of the microcatheter 120. The first and second elongated members 220, 216 can include a substantially circular and/or elliptical cross-section. The first and second lubricating jackets 221, 217 can include a substantially circular and/or elliptical cross-section corresponding to the cross-sections of their respective elongated members. The first and second elongated members 220, 216 can be concentrically positioned within the first and second lubricating jackets 221, 217, respectively. FIG. 2G illustrates an example configuration of the first and second elongated members 220, 216 within the lumen 122 of the microcatheter 120. The first and second elongated members 220, 216 can include a substantially horseshoe-shaped and/or an elliptical cross-section. The first and second lubricating jackets 221, 217 can include a substantially horseshoe-shaped and/or an elliptical cross-section corresponding to the cross-sections of their respective elongated members. The first and second elongated members 220, 216 can be concentrically positioned within the first and second lubricating jackets 221, 217, respectively.

FIG. 2H illustrates an example clot retrieval device 200 in a deployed configuration in a third position within a vessel 2 and in communication with a clot 1, as that configuration has been previously described. The retraction of the microcatheter 120 in a proximal direction can deploy the inner cage 208 and the outer cage 202. As a result, a portion of the clot 1 can be in communication with the outer cage 202 and/or the inner cage 208. Specifically, the portion of the clot 1 can be in communication with the network of inner struts 209 and/or the network of outer struts 203. The flow channel 208a of the inner cage 208 can allow fluid to flow beyond the clot 1. Additionally or alternatively, the first and second elongated members 220, 216 can be coupled at respective proximal ends 219, 215 of the first and second elongated members 220, 216 such that they move together. A clip 235 can be utilized to couple or decouple the first and second elongated members 220, 216, as will be discussed below. Alternatively, the clip 235 can be removed to decouple the first and second elongated members 220, 216, allowing the first and second elongated member 220, 216 to move independently of each other in a proximal and/or distal direction.

FIG. 2I illustrates an example clot retrieval device 200 in a pinched configuration within the vessel 2 and in communication with the clot 1. Additionally or alternatively, the first and second elongated members 220, 216 can be uncoupled at respective proximal ends 219, 215 of the first and second elongated members 220, 216 such that they move independently. Additionally or alternatively, the microcatheter 120 can be forwarded (e.g., resheathed) over the second elongated member 216 and/or the inner cage 208 such that network of inner struts 209 configured to form pinch cells 209a can pinch a portion of the clot 1. It can be advantageous for the for the first and second elongated member 220, 216 to move independently because the network of outer struts 203 can remain in communication and/or engaged with a portion of the clot 1 while the pinching cells 209a of the inner cage 208 can pinch a portion of the clot 1.

FIG. 2J depicts an example first elongated member 220 and an example second elongated member 216 including a taper. The first elongated member 220 can include a first plurality of segments 220a, 220b, 220c such that each segment of the plurality can include increasing respective outer diameters OD9, OD8, and OD7 such that the taper can be formed. The taper can be continuous, for example, can include an outer diameter at the proximal end 219 of the first elongated member 220 and a smaller outer diameter at the distal end 218 of the first elongated member 220. The first elongated member 220 can include a variable stiffness profile therealong, a proximal end 219 of the first elongated member 220 being stiffer than a distal end 219 of the first elongated member 220. The second elongated member 216 can include a first plurality of segments 216a, 216b, and 216c such that each segment of the plurality can include increasing respective outer diameters OD12, OD11, and OD10 such that the taper can be formed. The taper can be continuous, for example, can include an outer diameter at the proximal end 215 of the second shaft 216 and a smaller outer diameter at the distal end 214 of the second shaft 216. The second elongated member 216 can include a variable stiffness profile therealong, a proximal end 215 of the second elongated member 216 being stiffer than a distal end 214 of the second elongated member 216. Additionally or alternatively, only the second elongated member 216 includes a taper. Additionally or alternatively, only the first elongated member 220 includes a taper. In examples, the first and second elongated members 220, 216 include a taper.

In some examples, the first and second lubricating jackets 221, 217 can include a plurality of segments including a corresponding inner diameter dimensioned to substantially equal the outer diameters of each corresponding segment of the respective elongated member, thereby forming a taper of the lumen of each respective lubricating jacket. As an example, the lumen 221a of first lubricating jacket 221 can include a plurality of segments each including an inner diameter. A first segment of the first lubricating jacket 221 can correspond to the first segment, for example segment 220a, of the first elongated member 220 such that the inner diameter of the first segment of the first lubricating jacket 221 can be substantially equal to the outer diameter OD9. Alternatively, the first and second lubricating jackets can include respective constant inner diameters. Additionally or alternatively, the constant inner diameter of the first lubricating jacket 221 can be the same as the constant inner diameter of the second lubricating jacket 217. Additionally or alternatively, the constant inner diameter of the first lubricating jacket 221 can be different from the constant inner diameter of the second lubricating jacket 217.

FIG. 2K illustrates an example clip 235 of an example clot retrieval device 200. A clip 235 can include a first and second c-shaped features 236, 238 with a connective structure 239 therebetween. The first and second c-clips 236, 238 can be configured to receive the first and/or second elongated members 220, 216. Additionally, the first and second c-shaped features 236, 238 can be configured to receive the proximal ends 219, 215 of the first and/or second elongated members 220, 216. The c-shaped features 236, 238 can be made of stainless steel, plastic, and/or other suitable materials. The clip 235 can be configured to couple the first and second elongated members 220, 216 when engaged with the first and second c-shaped features 236, 238. The clip 235 can be configured to decouple the first and second elongated members 220, 216 when disengaged from the first and second c-shaped features 236, 238.

FIG. 3 is a flowchart depicting a method (300) for assembly of an example clot retrieval device. The method 300 can include, at block 302, patterning a first predetermined pattern on a first tube to form an outer cage (e.g., outer cage 102), the outer cage comprising an outer diameter (e.g., outer diameter OD1). At block 304, the method 300 can include patterning a second predetermined pattern on a second tube to form an inner cage (e.g., inner cage 108) comprising an inner flow channel (e.g., flow channel 108a), and at block 304, can include positioning the inner cage concentrically within the outer cage. Additionally or alternatively, the clot retrieval device (e.g., clot retrieval device 100) can include an expanded configuration with the outer diameter greater than an inner diameter (e.g., inner diameter ID1) of a microcatheter (e.g., microcatheter 120).

Additionally or alternatively, an outer diameter of the first tube can be approximately equal to the outer diameter of the clot retrieval device in an expanded configuration, thereby expanding an outer cage to a greater diameter under a clot (e.g., clot 1) or to improve vessel wall (e.g., vessel 2) apposition when compared to an outer cage of a smaller diameter shape set to attain the outer diameter of the clot retrieval device, when both clot retrieval devices have equal radial force.

Additionally or alternatively, an outer diameter of the first tube can be greater than the outer diameter of the clot retrieval device in an expanded configuration, thereby expanding an outer cage to a greater diameter under a clot or to improve vessel wall apposition when compared to an outer cage of a smaller diameter shape set to attain the outer diameter of the clot retrieval device, when both clot retrieval devices have equal radial force.

Additionally or alternatively, the network of outer struts 103 of the outer cage 102 can include a pre-determined pattern disposed thereon including eight struts distributed, uniformly or non-uniformly, radially forming a ring-like pattern as discussed in detail below. However, greater or fewer struts can be included as needed or required. Additionally or alternatively, the network of inner struts 109 of the inner cage 108 can include a pre-determined pattern disposed thereon including four struts which can be uniformly or non-uniformly distributed radially to form a ring-like pattern as discussed below. However, greater or fewer struts can be included as needed or required.

Additionally or alternatively, the method 300 can include attaching a first radiopaque marker (e.g., distal radiopaque band 128b) at a distal end (e.g., distal end 106) of the outer cage. Additionally or alternatively, the method 300 can include attaching a second radiopaque marker (e.g., proximal radiopaque marker 128a) at a proximal end (e.g., proximal end 104) of the outer cage.

Additionally or alternatively, the method 300 can include attaching a first elongated member (e.g., first elongated member 114) to a proximal end of the outer cage. The first elongated member can be configured to move the outer cage between delivery and expanded configurations. Additionally or alternatively, the method 300 can include attaching a second elongated member (e.g., second elongated member 118) to a proximal end of the inner cage. The second elongated member can be configured to move the inner cage between delivery and expanded configurations. Additionally or alternatively, the first elongated member can be a tube. Additionally or alternatively, the second elongated member can be a wire.

Additionally or alternatively, the second elongated member can include a first plurality of segments (e.g., the first plurality of segments 114a, 114b) such that each segment of the plurality can include increasing respective outer diameters (e.g., OD5, OD6) such that a taper can be formed. Additionally or alternatively, the second elongated member can include a variable stiffness profile therealong, a proximal end (e.g., proximal end 113b) of the second elongated member being stiffer than a distal end (e.g., distal end 119a) of the second elongated member. Additionally or alternatively, the first and second elongated members can be within separate lumens within the microcatheter.

Additionally or alternatively, the method 300 can include attaching a distal end (e.g., 119a) of the second elongated member to a proximal end (e.g., proximal end 116a) of a receptacle (e.g., receptacle 116). Additionally or alternatively, the method 300 can include attaching the proximal end (e.g., proximal end 110) of the inner cage within a cavity (e.g., cavity 116b) of the receptacle. Additionally or alternatively, the second elongated member can be slidable within a lumen (e.g., lumen 115) of the first elongated member. Additionally or alternatively, the receptacle can include a step (e.g., step 116c) within the cavity to prevent over insertion of the proximal end of the inner cage.

Additionally or alternatively, the method 300 can include patterning a third pre-determined pattern on the first elongated member to achieve a desired stiffness profile along the first elongated member. Additionally or alternatively, the third pre-determined pattern can include one or more of a spiral pattern (e.g., spiral pattern 126a), one or more interrupted spiral patterns (e.g., interrupted spiral patterns 126b), or one or more radial cut patterns (e.g., radial cut patterns 126c).

Additionally or alternatively, the method 300 can include uncoupling the first and second elongated members (e.g., first and second elongated member 216, 220), and forwarding, proximally, the microcatheter over the inner cage causing cells (e.g., pinching cells 209a) of the inner cage to collapse on the clot exerting additional pressure on that portion of the clot or by causing the clot to become engaged between the distal end of the microcatheter and a cell of the inner cage.

Additionally or alternatively, the method 300 can include coupling, using a clip (e.g., clip 235) comprising c-shaped features (e.g., first and second c-shaped features 236, 238), the first and second elongated members (e.g., first and second elongated member 216, 220) by attaching, using the c-shaped features, the proximal end (e.g., proximal ends 215, 219) of the first and second elongated members respectively, and sliding, distally or proximally, the first and second elongated member in unison.

Figure 4:
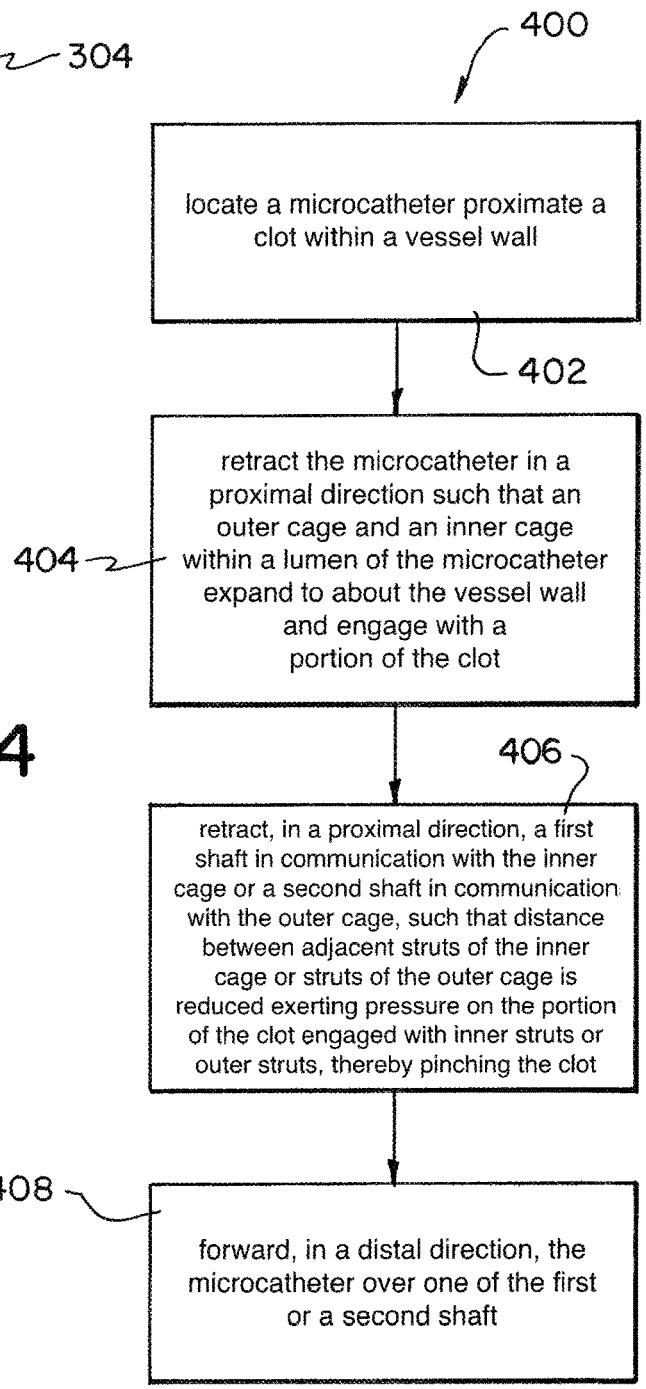
FIG. 4 is a flowchart depicting operation an example clot retrieval device.

FIG. 4 is a flowchart depicting operation an example clot retrieval device. The method 400 can include, at block 402, locating a microcatheter (e.g., microcatheter 120) proximate a clot (e.g., clot 1) within a vessel (e.g., vessel 2). At block 404, the method 400 can include retracting the microcatheter in a proximal direction such that an outer cage (e.g., outer cage 102) and an inner cage (e.g., inner cage 108) within a lumen (e.g., lumen 122) of the microcatheter expand to about the vessel wall and engage with a portion of the clot. At block 406, the method 400 can include retracting, in a proximal direction, a first elongated member (e.g., second elongated member 118) in communication with the inner cage or a second elongated member (e.g., first elongated member 114) in communication with the outer cage, such that distance between adjacent struts (e.g., network of inner struts 209) of the inner cage or struts (e.g., network of outer struts 103) of the outer cage is reduced exerting pressure on the portion of the clot engaged with inner struts or outer struts, thereby pinching the clot. At block 408, the method 400 can include forwarding, in a distal direction, the microcatheter over one of the first or a second elongated members. Additionally or alternatively, forwarding the microcatheter pinches a portion of the clot by causing cells (e.g., pinching cells 109a) of the inner cage to collapse on the clot exerting additional pressure on that portion of the clot or by causing the clot to become engaged between the distal end of the microcatheter and a cell of the inner cage.

Additionally or alternatively, the method 400 can include coupling, using a clip (e.g., clip 235) including c-shaped features (e.g., first and second c-shaped features 236, 238), the first and second elongated members by attaching, using the c-shaped features, the proximal end of the first and second elongated members respectively. Additionally, sliding, distally or proximally, the first and second elongated member in unison.

Additionally or alternatively, the method 400 can include retracting the microcatheter, the first and second elongated members, the inner and outer cage, and the clot from the vessel wall. Additionally or alternatively, the network of outer struts 103 of the outer cage 102 can include a pre-determined pattern disposed thereon including eight struts distributed uniformly radially forming a ring-like pattern as discussed in detail below. However, greater or fewer struts can be included as needed or required. Additionally or alternatively, the network of inner struts 109 of the inner cage 108 can include a pre-determined pattern disposed thereon including four struts which can be uniformly or non-uniformly distributed radially in to form a ring-like pattern as discussed below. However, greater or fewer struts can be included as needed or required.

Additionally or alternatively, retracting the first elongated member in communication with the inner cage can include uncoupling the first and second elongated members from one another such that the first elongated member can be retracted independently of the second elongated member. Additionally or alternatively, the second elongated member can be a tube. Additionally or alternatively, the first elongated member can be a wire.

Additionally or alternatively, the first and second elongated members can be within separate lumens (e.g., lumen 221a and lumen 217a) of first and second jackets (e.g., first and second lubricating jackets 221, 217) within the microcatheter. Additionally or alternatively, the second elongated member can include a first plurality of segments such that each segment of the plurality can include decreasing respective outer diameters such that a taper is formed and the second elongated member comprises a variable stiffness profile therealong, a proximal end of the second elongated member being stiffer than a distal end of the second elongated member.

Additionally or alternatively, retracting the first elongated member in communication with the inner cage further can include sliding, in a proximal or distal direction, the first elongated member within a lumen of the second elongated member.

Additionally or alternatively, the third pre-determined pattern can be a spiral cut (e.g., spiral cut 126a) can be a helix having a uniform spacing between each revolution of the helix and/or a uniform helix angle forming the uniform spacing between each revolution of the helix along a length of the first or second elongated member. Additionally or alternatively, the spiral cut (e.g., spiral cut 126a) can be a helix having non-uniform spacing between each revolution of the helix and/or a non-uniform helix angle forming the non-uniform spacing between each revolution of the helix along a length of the first or second elongated member. Additionally or alternatively, the third pre-determined pattern can be an interrupted spiral pattern (e.g., interrupted spiral pattern 126b) disposed thereon. The interrupted spiral pattern can be a helix cut having a uniform spacing between each revolution of the helix and/or a uniform helix angle forming the uniform spacing between each revolution of the helix along a length of the first or second elongated member.

Additionally or alternatively, the interrupted spiral pattern can be a helix cut having a non-uniform spacing between each revolution of the helix and/or a non-uniform helix angle forming the non-uniform spacing between each revolution of the helix along a length of the first or second elongated member. The helix cut need not be a continuous cut, said differently, there can be a plurality of cuts interrupted, or separated, by material of the first or second elongated member. Additionally or alternatively, the third pre-determined pattern can be a radial cut pattern (e.g., radial pattern 126c) disposed thereon. The radial pattern can be a plurality of cuts perpendicular to the length of the first or second elongated member and repeated uniformly in along a length of the first or second elongated member. Additionally or alternatively, the radial pattern can be a plurality of cuts perpendicular to the length of the first or second elongated member and repeated non-uniformly in along a length of the first or second elongated member.

The disclosure is not limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician.

In describing examples, terminology is resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 71% to 99%.

By "comprising" or "containing" or "including" or "having" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise. Ranges can be expressed herein as from "about" or "approximately" one particular value and/or to "about" or "approximately" another particular value. When such a range is expressed, other exemplary embodiments include from the one particular value and/or to the other particular value.

The descriptions contained herein are examples of the disclosure and are not intended in any way to limit the scope of the disclosure. While particular examples of the present disclosure are described, various modifications to devices and methods can be made without departing from the scope and spirit of the disclosure. For example, while the examples described herein refer to particular components, the disclosure includes other examples utilizing various combinations of components to achieve a described functionality, utilizing alternative materials to achieve a described functionality, combining components from the various examples, combining components from the various example with known components, etc. The disclosure contemplates substitutions of component parts illustrated herein with other well-known and commercially-available products. To those having ordinary skill in the art to which this disclosure relates, these modifications are often apparent and are intended to be within the scope of the claims which follow.

What is claimed is:

1. A method for removing a clot, the method comprising:
locating a microcatheter proximate a clot within a vessel;
retracting the microcatheter in a proximal direction such that an outer cage and an inner cage within a lumen of the microcatheter expand to abut a vessel wall and engage with a portion of the clot;
retracting, in a proximal direction, a first elongated member in communication with the outer cage or a second elongated member in communication with the inner cage, such that a distance between adjacent struts of the inner cage or struts of the outer cage is reduced to exert pressure on the portion of the clot engaged with inner struts or outer struts, thereby pinching the clot;
forwarding, in a distal direction, the microcatheter over one of the first elongated member or the second elongated member;
wherein forwarding the microcatheter pinches a portion of the clot by causing cells of the inner cage to collapse on the clot exerting additional pressure on that portion of the clot or by causing the clot to become engaged between the distal end of the microcatheter and a cell of the inner cage,
wherein the outer cage has a proximal end connected to a first collar and a distal end;
wherein the inner cage has a proximal end connected to a second collar and a distal end, the inner cage concentrically positioned within the outer cage;
wherein the first elongated member is located within a first lumen of the microcatheter and having a proximal end and a distal end; and
wherein the second elongated member is located within a second lumen of the microcatheter and having a proximal end and a distal end,
wherein the inner cage and the outer cage have a delivery configuration and an expanded configuration,
wherein, in the expanded configuration, the proximal end of the outer cage is proximal of and approximate the proximal end of the inner cage and the distal end of the outer cage is distal of and approximate the distal end of the inner cage,
wherein the second lumen is located adjacent the first lumen,
wherein the distal end of the first elongated member comprises:
a step that abuts the first collar; and
a positioning pin located distal of the step,
wherein the positioning pin is slidably disposed within a lumen of the first collar such that a distal translation of the first elongated member moves the outer cage distally and a proximal translation of the first elongated member disengages the step from the first collar and slides the positioning pin from the lumen of the first collar such that the outer cage does not move proximally, and
wherein the distal end of the second elongated member comprises:
a step that abuts or is attached to the second collar; and
a guide pin located distal of the step,
wherein the guide pin is attached to the second collar such that a distal translation of the second elongated member moves the inner cage distally and a proximal translation of the second elongated member moves the inner cage proximally.

2. The method of claim 1, the method further comprising:
retracting the microcatheter, the first and second elongated members, the inner and outer cage, and the clot from the vessel wall.

3. The method of claim 1, wherein locating the microcatheter proximate the clot further comprises:
coupling, using a clip comprising c-shaped features, the first and second elongated members by:
attaching, using the c-shaped features, a proximal end of the first and second elongated members respectively; and
sliding the microcatheter and the first and second elongated member in unison towards and proximate to the clot.

4. The method of claim 1, wherein retracting the first elongated member in communication with the inner cage further comprises:
uncoupling the first and second elongated members from one another such that the first elongated member can be retracted independently of the second elongated member.

5. The method of claim 1, wherein the first and second elongated members are within separate lumens of first and second jackets within the microcatheter.

6. The method of claim 1,
wherein the second elongated member comprises a first plurality of segments such that each segment of the plurality comprising decreasing respective outer diameters such that a taper is formed and the second elongated member comprises a variable stiffness profile therealong, a proximal end of the second elongated member being stiffer than a distal end of the second elongated member.

7. The method of claim 1, wherein retracting the first elongated member in communication with the inner cage further comprises:
sliding, in a proximal or distal direction, the first elongated member within a lumen of the second elongated member.

8. The method of claim 1, wherein a pre-determined pattern is patterned on the second elongated member to achieve a desired stiffness profile along the second elongated member.

9. A clot retrieval device comprising:
a microcatheter;
an outer cage having a proximal end connected to a first collar and a distal end;
an inner cage having a proximal end connected to a second collar and a distal end, the inner cage concentrically positioned within the outer cage;
a first elongated member in communication with the outer cage, the first elongated member located within a first lumen of the microcatheter and having a proximal end and a distal end; and
a second elongated member in communication with the inner cage, the second elongated member located within a second lumen of the microcatheter and having a proximal end and a distal end,
wherein the clot retrieval device has a delivery configuration and an expanded configuration,
wherein, in the expanded configuration, the proximal end of the outer cage is proximal of and approximate the proximal end of the inner cage and the distal end of the outer cage is distal of and approximate the distal end of the inner cage,
wherein the second lumen is located adjacent the first lumen,
wherein the distal end of the first elongated member comprises:
a step that abuts the first collar; and
a positioning pin located distal of the step,
wherein the positioning pin is slidably disposed within a lumen of the first collar such that a distal translation of the first elongated member moves the outer cage distally and a proximal translation of the first elongated member disengages the step from the first collar and slides the positioning pin from the lumen of the first collar such that the outer cage does not move proximally, and
wherein the distal end of the second elongated member comprises:
a step that abuts or is attached to the second collar; and
a guide pin located distal of the step,
wherein the guide pin is attached to the second collar such that a distal translation of the second elongated member moves the inner cage distally and a proximal translation of the second elongated member moves the inner cage proximally.

10. The clot retrieval device of claim 9, wherein an outer diameter of the outer cage is approximately equal to an outer diameter of the clot retrieval device in the expanded configuration, thereby expanding the outer cage to a greater diameter under a clot or to improve vessel wall apposition when compared to an outer cage of a second smaller diameter clot retrieval device that is shapeset to attain the outer diameter of the clot retrieval device, when both clot retrieval devices have equal radial force.

11. The clot retrieval device of claim 9, wherein an outer diameter of the outer cage is greater than the outer diameter of the clot retrieval device in the expanded configuration, thereby expanding the outer cage to a greater diameter under a clot or to improve vessel wall apposition when compared to an outer cage of a second smaller diameter clot retrieval device that is shapeset to attain the outer diameter of the clot retrieval device, when both clot retrieval devices have equal radial force.

12. The clot retrieval device of claim 9, wherein the outer cage is patterned such that it comprises a ring of eight struts.

13. The clot retrieval device of claim 9, wherein the inner cage is patterned such that it comprises a ring of four struts configured to pinch a portion of a clot.

14. The clot retrieval device of claim 9, further comprising:
a clip comprising c-shaped features at each end of the clip, each feature configured to receive one of: the first elongated member or the second elongated member, the clip configured to couple the first and second elongated member when attached.

15. The clot retrieval device of claim 9, wherein:
the first elongated member is configured to move the outer cage between delivery and expanded configurations; and
the second elongated member is configured to move the inner cage between delivery and expanded configurations.

16. The clot retrieval device of claim 15,
wherein the second elongated member comprises a first plurality of segments such that each segment of the plurality comprising decreasing respective outer diameters such that a taper is formed and the second elongated member comprises a variable stiffness profile therealong, a proximal end of the second elongated member being stiffer than a distal end of the second elongated member.

17. The clot retrieval device of claim 15, further comprising:
a pre-determined pattern on the first elongated member to achieve a desired stiffness profile along the first elongated member.

18. The clot retrieval device of claim 15, wherein the first and second elongated member are within respective lumens of a first and second lubricated elongated member jackets within a microcatheter.

* * * * *